(12) United States Patent
Ianchulev

(10) Patent No.: US 10,905,591 B1
(45) Date of Patent: Feb. 2, 2021

(54) METHODS AND DEVICES FOR INCREASING AQUEOUS DRAINAGE OF THE EYE

(71) Applicant: Tsontcho Ianchulev, Harrison, NY (US)

(72) Inventor: Tsontcho Ianchulev, Harrison, NY (US)

(*) Notice: Subject to any disclaimer, the term of this patent is extended or adjusted under 35 U.S.C. 154(b) by 0 days.

(21) Appl. No.: 16/719,727

(22) Filed: Dec. 18, 2019

Related U.S. Application Data

(63) Continuation of application No. 16/699,039, filed on Nov. 28, 2019.

(60) Provisional application No. 62/876,799, filed on Jul. 22, 2019.

(51) Int. Cl.
*A61F 9/007* (2006.01)

(52) U.S. Cl.
CPC ................................ *A61F 9/00781* (2013.01)

(58) Field of Classification Search
CPC ............................ A61F 9/00781; A61F 9/007
See application file for complete search history.

(56) References Cited

U.S. PATENT DOCUMENTS

| | | | |
|---|---|---|---|
| 5,437,678 A | 8/1995 | Sorensen | |
| 6,979,328 B2 | 12/2005 | Baerveldt et al. | |
| 7,207,980 B2 | 4/2007 | Christian et al. | |
| 7,465,310 B2 | 12/2008 | Isogimi | |
| 7,699,882 B2 | 4/2010 | Stamper et al. | |
| 7,785,321 B2 | 8/2010 | Baerveldt et al. | |
| 7,842,034 B2 | 11/2010 | Mittelstein et al. | |
| 7,959,641 B2 | 6/2011 | Sorensen et al. | |
| 7,967,772 B2 | 6/2011 | McKenzie et al. | |
| 8,034,105 B2 | 10/2011 | Stegmann et al. | |
| 8,123,729 B2 | 2/2012 | Yamamoto et al. | |
| 8,172,830 B2 | 5/2012 | Christian et al. | |
| 8,267,882 B2 | 9/2012 | Euteneuer et al. | |
| 8,348,924 B2 | 1/2013 | Christian et al. | |
| 8,425,473 B2 | 4/2013 | Ho et al. | |
| 8,491,549 B2 | 7/2013 | Conston et al. | |

(Continued)

FOREIGN PATENT DOCUMENTS

WO  WO-00/64389 A1  11/2000

OTHER PUBLICATIONS

International Search Report and Written Opinion issued in corresponding International Application No. PCT/US2020/042594, dated Dec. 3, 2020 (Dec. 3, 2020). 10 pages.

*Primary Examiner* — Ophelia A Hawthorne
*Assistant Examiner* — Heather K Barnwell
(74) *Attorney, Agent, or Firm* — Mintz Levin Cohn Ferris Glovsky and Popeo, P.C.

(57) ABSTRACT

Devices and methods to remove trabecular meshwork to treat glaucoma and other conditions which may not utilize cutting elements when stripping the trabecular meshwork. The trabeculorhexis parts tissue by applying non-cutting shear and tension to the tissue to disinsert the tissue from its attachments. Reducing or eliminating the need for sharp cutting implements in the eye reduces the likelihood of incisional bleeding, iris and scleral tissue maceration and further inadvertent tissue damage of the gonio structure of the eye. In another aspect, a cutting element may be used to form a circumferential slit in a wall of Schlemm's canal in conjunction with removal of trabecular meshwork or independently.

30 Claims, 18 Drawing Sheets

(56) References Cited

U.S. PATENT DOCUMENTS

| | | |
|---|---|---|
| 8,512,321 B2 | 8/2013 | Baerveldt et al. |
| 8,529,494 B2 | 9/2013 | Euteneuer et al. |
| 8,721,656 B2 | 5/2014 | De Juan, Jr. et al. |
| 8,894,603 B2 | 11/2014 | Badawi et al. |
| 9,066,783 B2 | 6/2015 | Euteneuer et al. |
| 9,095,412 B2 | 8/2015 | Badawi et al. |
| 9,107,729 B2 | 8/2015 | Sorensen et al. |
| 9,216,109 B2 | 12/2015 | Badawi et al. |
| 9,226,850 B2 | 1/2016 | Baerveldt et al. |
| 9,358,155 B2 | 6/2016 | Sorensen et al. |
| 9,693,902 B2 | 7/2017 | Euteneuer et al. |
| 9,757,279 B2 | 9/2017 | Kahook |
| 9,820,883 B2 | 11/2017 | Berlin |
| 9,820,885 B2 | 11/2017 | Sorensen et al. |
| 9,855,167 B2 | 1/2018 | Badawi et al. |
| 9,872,799 B2 | 1/2018 | Kahook |
| 9,895,258 B2 | 2/2018 | Badawi et al. |
| 9,999,544 B2 | 6/2018 | Baerveldt et al. |
| 10,085,885 B2 | 10/2018 | Baerveldt et al. |
| 10,123,905 B2 | 11/2018 | Mittelstein et al. |
| 10,179,066 B2 | 1/2019 | Badawi et al. |
| 10,327,947 B2 | 6/2019 | Kahook |
| 2003/0236484 A1 | 12/2003 | Lynch et al. |
| 2006/0047263 A1 | 3/2006 | Tu et al. |
| 2006/0241580 A1 | 10/2006 | Mittelstein et al. |
| 2007/0073275 A1 | 3/2007 | Conston et al. |
| 2009/0287143 A1 | 11/2009 | Line |
| 2009/0287233 A1 | 11/2009 | Huculak |
| 2010/0262174 A1 | 10/2010 | Sretavan et al. |
| 2012/0035524 A1 | 2/2012 | Silvestrini |
| 2013/0253402 A1 | 9/2013 | Badawi et al. |
| 2013/0289545 A1 | 10/2013 | Baerveldt et al. |
| 2015/0045820 A1 | 2/2015 | Kahook |
| 2016/0100980 A1 | 4/2016 | Badawi et al. |
| 2016/0287438 A1 * | 10/2016 | Badawi ................ A61K 31/728 |
| 2017/0252212 A1 | 9/2017 | Euteneuer et al. |
| 2017/0258636 A1 | 9/2017 | Baerveldt et al. |
| 2017/0367890 A1 | 12/2017 | Kahook |
| 2018/0125712 A1 | 5/2018 | Sorensen et al. |
| 2018/0133056 A1 | 5/2018 | Kahook |
| 2018/0147088 A1 | 5/2018 | Liang et al. |
| 2018/0271699 A1 | 9/2018 | Badawi et al. |
| 2018/0289544 A1 | 10/2018 | Baerveldt et al. |
| 2018/0360655 A1 | 12/2018 | Berlin |
| 2018/0360661 A1 * | 12/2018 | Kahook .............. A61F 9/00745 |
| 2019/0060119 A1 | 2/2019 | Baerveldt et al. |
| 2019/0142632 A1 | 5/2019 | Badawi et al. |

* cited by examiner

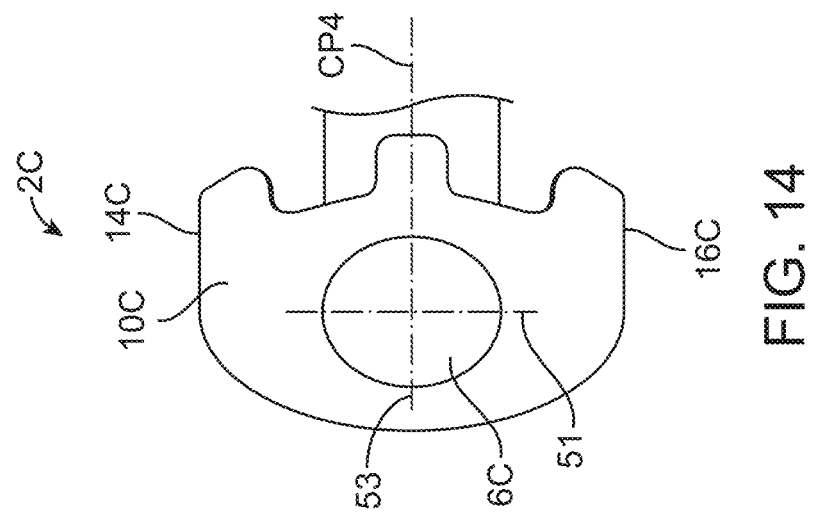
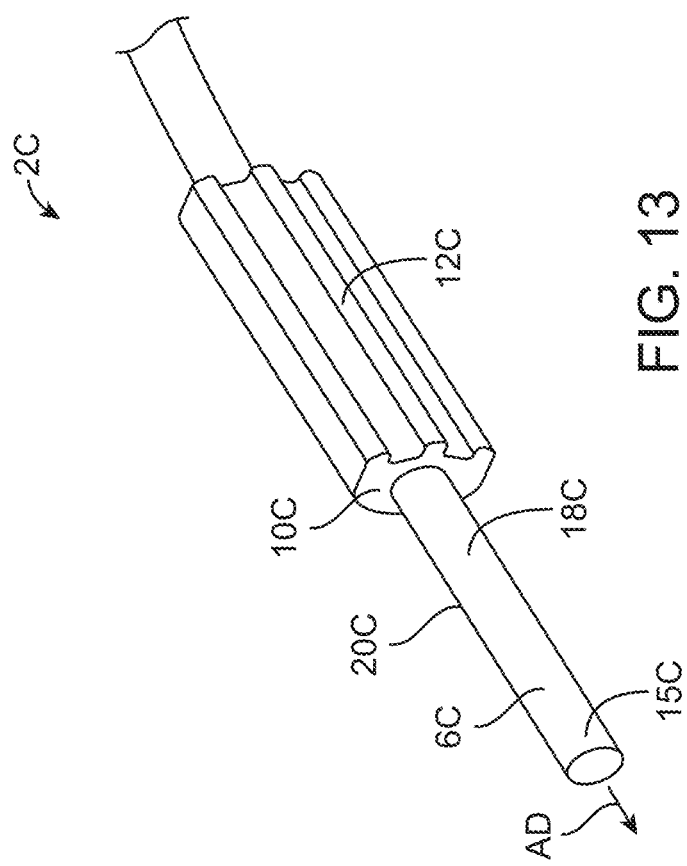
FIG. 13
FIG. 14

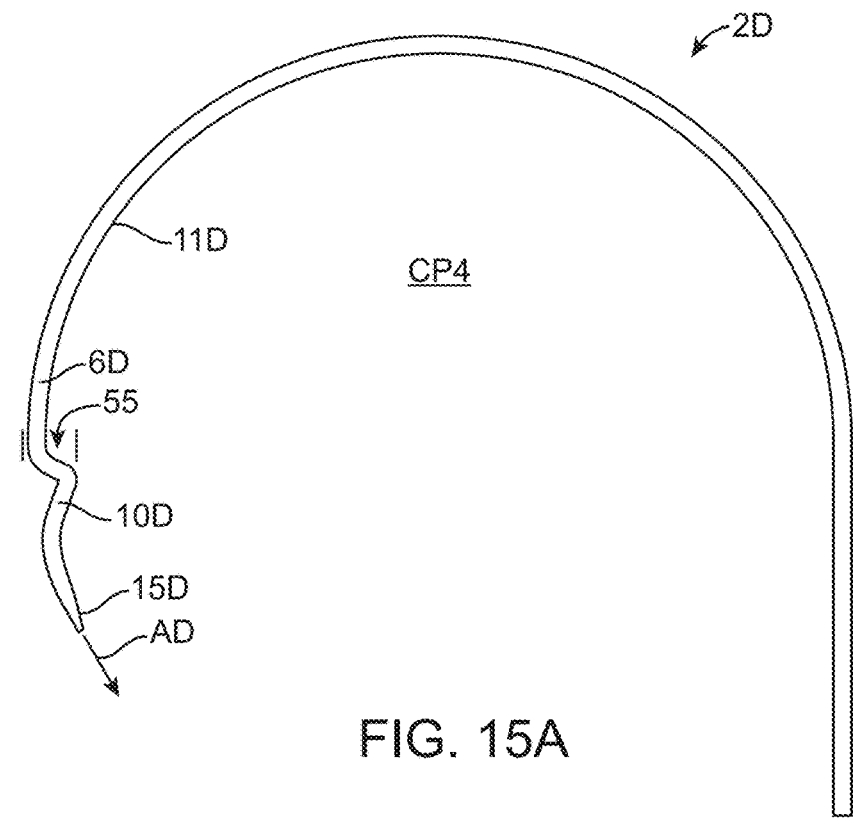
FIG. 15A
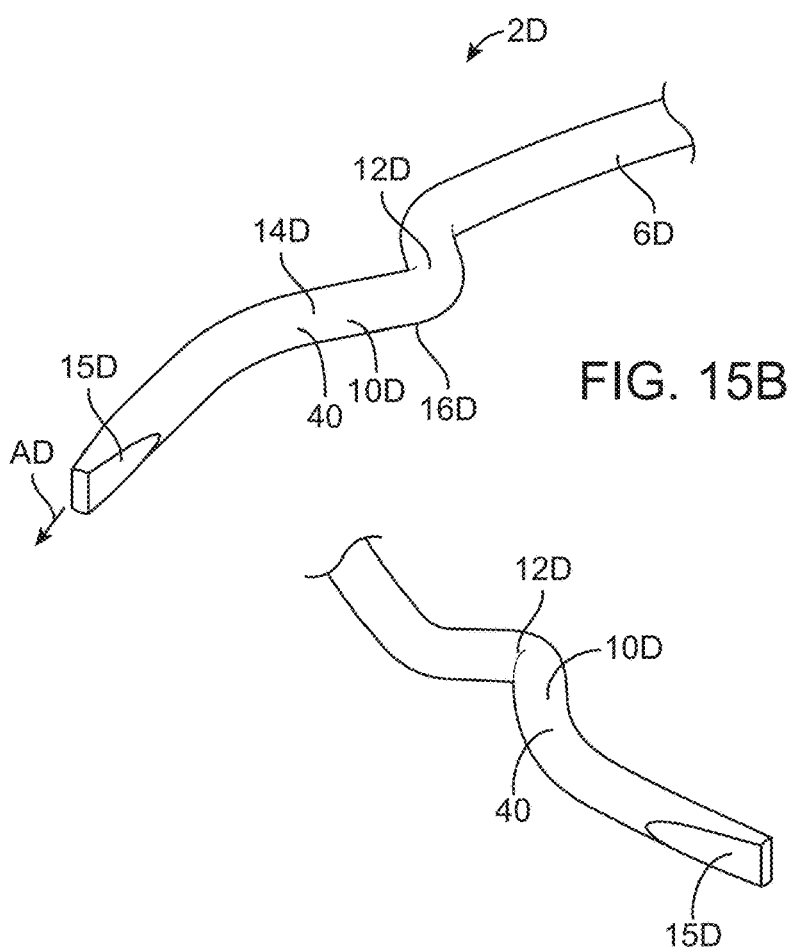
FIG. 15B
FIG. 15C

METHODS AND DEVICES FOR INCREASING AQUEOUS DRAINAGE OF THE EYE

CROSS-REFERENCE TO RELATED APPLICATIONS

This application is a continuation of co-pending U.S. application Ser. No. 16/699,039, filed Nov. 28, 2019, which claims the benefit of priority under 35 U.S.C. 119(e) to U.S. Provisional Patent Application Ser. No. 62/876,799, filed Jul. 22, 2019. The disclosures are hereby incorporated by reference in their entireties.

BACKGROUND OF THE INVENTION

The present invention is directed to methods and devices for increasing aqueous drainage of the eye. In one specific application, for example, the devices and methods may be used to remove trabecular meshwork (with or without part of Schlemm's canal) to treat glaucoma and other conditions.

Current trabecular excision devices typically use excisional blades or sharp needles (e.g. goniotomy) which have been around for decades. These devices typically create single stab-like partial cuts of the trabecular meshwork. More recent devices such as the Kahook dual blade (U.S. Pat. No. 9,872,799), Baerveldt (U.S. Pat. No. 9,999,544) and the cauterizing/plasma cutting blades of the Trabectome (U.S. Pat. No. 9,820,885), all have a sharp incisional or ablative cutting surface. As such, they all suffer from the major clinical disadvantage related to the sharp cutting nature in the process of tissue engagement. The sharp blades often create interrupted, discontinuous and incongruous cuts of the inner canal wall which are imprecise and more akin to tissue maceration rather than the desired tissue extraction with non-lacerating atraumatic removal. This is also often associated with significant bleeding and collateral damage of both sclera, endothelium and iris tissue. Furthermore, a single cutting blade may simply open the trabecular meshwork without removing much material. In order to remove material, some prior art devices provide two spaced-apart cutting elements (side by side) in an attempt to remove material between the cutting elements.

Prior art excision ab interno devices are also typically limited to straight rigid intraocular shafts connected to a cutting element in a fixed orientation relative to the shaft. A problem with these devices is that complex motion is required to advance the cutting element. The distal end of the shaft must be moved longitudinally and laterally to follow the curved shape while also changing the angle of the shaft relative to the canal. Even when the complex motions are coordinated, another challenging aspect related to prior art devices having rigid shafts is that the orientation of the cutting element may not follow the contour of Schlemm's canal as desired.

SUMMARY OF THE INVENTION

The present invention provides methods and devices for increasing aqueous drainage of the eye. In some methods and devices of the present invention, tissue is removed from the eye to increase aqueous drainage. In one aspect, the present methods and devices may not utilize cutting elements when stripping the trabecular meshwork. The long-term stability of incised tissue surfaces can be significantly reduced compared to a blunt tissue rhexis which is characterized by deeper and at times a more natural disinsertion of the meshwork fibril roots from their lateral attachment at the origin. This aspect may be characterized as a "trabeculorhexis" in which trabecular meshwork and Schlemm's canal tissue is parted by applying non-cutting shear and tension to the tissue to tear the tissue and, at times, disinsert the tissue from its attachments. Reducing or eliminating the need for sharp cutting implements in the eye reduces the likelihood of incisional bleeding, iris and scleral tissue maceration and further inadvertent tissue damage of the gonio structure of the eye.

In a further aspect of the present invention, the device includes a tissue engager which may be a non-cutting blunt probing element attached to a shaft. A guide member extends distally from the tissue engager which is intended to guide the non-cutting tissue engager along the Schlemm's canal to allow for smooth continuous trabecular meshwork removal (including disinsertion). The shaft may be made of a super-elastic material and the tissue engager may tear a strip of the TM along a continuous segment of Schlemm's canal.

In still another aspect, the device includes a flexible shaft which may be extended and retracted from the handpiece. The shaft is curved, or can assume a curved memory shape/contour, to naturally change the angle of the tissue engager relative to the handpiece as the shaft is extended longitudinally from the handpiece. The shaft may change the angle of the tissue engager relative to the handpiece by at least 45 degrees when the shaft is extended from the handpiece. The shaft may be flexible and may be deformed during use to provide a spring load on the tissue engager. For example, the shaft may be resilient relative to forces exerted in an advancing direction so that the shaft develops a spring load in the advancing direction. The shaft may also be resilient in a direction perpendicular to the advancing direction and lying in the plane of curvature. Thus, the shaft may develop a spring load in use which has a component in the advancing direction and a component in a radially outward direction relative to the axis of the eye. The shaft is shaped to apply a radially outward force on the tissue relative to the axis of the eye when the tissue engager is moved through the trabecular meshwork which may help stabilize the device as it is advanced.

The device includes an elongate shaft coupled to a handpiece. An actuator is coupled to the elongate shaft to extend and retract the shaft. A main body is coupled to the shaft. The main body comprises a tissue engager which is used to disrupt and displace the trabecular network. A guide member extends distally from the main body and is positioned and advanced through Schlemm's canal during use. The guide member is sized and configured to be positioned adjacent a wall of Schlemm's canal to guide advancement of the tissue engager in an advancing direction to displace the trabecular meshwork.

The guide member may be part of the shaft which extends beyond a distal end of the main body. Stated another way, the elongate shaft may extend distally from tissue engager to form at least part of the guide member and may define a distal end of the guide member. The guide member may extend distally 300 to 5000 microns from the main body and has an upper side and a lower side. The lower side of the guide member slides against a wall of Schlemm's canal. The upper surface is configured to gather the tissue as the tissue engager moves through the trabecular meshwork during use.

The upper surface is spaced apart from the lower surface by 250 to 550 microns or by 250 to 450 microns when measured at a center of the upper surface with the center of the upper surface being the furthest part of the upper surface from the lower surface. The upper surface may have a radius of curvature of 100 to 350 microns or even 50 to 300 microns. In some embodiments, the upper surface is defined at least partially by the elongate shaft.

The upper surface may have a radius of curvature less than a radius of curvature of the lower surface. The upper surface may have a convex surface formed by the elongate shaft. The lower surface may be rounded with a radius of curvature of 400 to 750 microns when viewed along the advancing direction.

The tissue engager has a height measured perpendicular to the advancing direction which may be at least 150 microns and may be 500 to 800 microns. The tissue engager also has a width measured perpendicular to the advancing direction which may be at least 450 microns, 450-850 microns or 500-700 microns.

The tissue engager has a tissue engaging surface with a concave portion when viewed perpendicular to the advancing direction. The concave portion has an upper lip and a lower lip with the upper lip forming an angle of less than 90 degrees, and may be 30-70 degrees, with the advancing direction when viewed perpendicular to the advancing direction. The lower lip forms an angle of 0-30 degrees with the advancing direction when viewed perpendicular to the advancing direction. The concave portion forms a recess (when viewed in the advancing direction) having a depth of at least 50 microns, at least 100 microns or at least 200 microns and may be 300-600 microns.

The recess has a recess height measured perpendicular to the advancing direction and parallel to the central plane, the recess height being at least 200 microns and may be 300-600 microns. The recess also has a recess width measured perpendicular to the advancing direction and to a central plane which may be 300 to 700 microns or 400 to 600 microns. In some embodiments, the recess may be partially defined by a convex shaped portion of the elongate shaft.

The shaft extends proximally from the main body at an angle greater than 90 degrees, or even greater than 135 degrees, to the advancing direction and may even be at an angle of 160 to 200 degrees relative to the advancing direction.

The tissue engager has a first sidewall and a second sidewall extending from the tissue engaging surface on opposing lateral sides. The leading edges of the first and second sidewalls may be used to displace tissue during use with the material between the two lateral sides may be released from connection to the native tissue for removal. Gathering tissue between the first and second sidewalls and displacing the gathered tissue helps to ensure that material is removed rather than merely forming a slit.

The tissue engager defines a central plane on which the advancing direction lies. The first sidewall and the second sidewall may form an angle with a central plane of less than 45 degrees or even less than 30 degrees. In some embodiments, the tissue engager gathers tissue and displaces the tissue with the tissue engager as the tissue engager is advanced so that the tissue engager has a blunt engagement with the tissue. Blunt engagement helps to ensure that the tissue shears along the first sidewall and the second sidewall due to displacement of tissue gathered by the tissue engager.

The tissue engager may shear tissue without cutting the tissue so that the tissue engager is a blunt, non-incisional probe. In other embodiments, the tissue engager may include a cutting element without departing from numerous aspects of the present invention. When using blunt engagement, the tissue engager compresses and gathers tissue to bunch the tissue in a direction perpendicular to the advancing direction (and lying generally in a central plane). The tissue engager compresses and gathers tissue while the tissue is torn along the first sidewall and the second sidewall due to displacement of the gathered tissue.

The tissue engager may have a tissue engaging surface (proximal to the guide member) which contacts and displaces the tissue without cutting the tissue. The tissue engaging surface may have an orientation which is within 15 degrees, or even within 10 degrees, of perpendicular to the advancing direction will help gather tissue for displacement.

The tissue engager and shaft are shaped and configured to be capable of continuous advancement along Schlemm's canal along an angle of 30-120 degrees of the canal. The shaft may be made of any suitable material such as a superelastic material like nitinol. The shaft may have a curved shape with a radius of curvature of 5.0 to 9.0 mm and the curved shape may extending for 160 to 270 degrees.

The tissue engaging surface may have a width of at least 400 microns or may be in a range of 500-800 microns. The tissue engaging surface may have a height of at least 400 microns, at least 500 microns or within a range of 550-1000 microns.

The elongate shaft may have a cross-sectional shape with a minor axis and a major axis. The major axis may be within 30 degrees, or even within 15 degrees, of perpendicular to the central plane. The major axis may be at least 20% larger than the minor axis and the minor axis may be less than 250 microns while the major axis is larger than 250 microns.

The elongate shaft is advanced essentially longitudinally to advance the tissue engager through the trabecular meshwork. Furthermore, the curved shape of the shaft causes the shaft to naturally follow the shape of the canal thereby greatly reducing the necessary manipulations compared to prior art devices. The tissue engager is configured for introduction into the eye ab interno. The shaft extends through a lumen in an introducer. The introducer has a curved tip (which is curved by 15-60 degrees) to facilitate introduction of the guide member into the canal.

The shaft is coupled to a handpiece having an actuator. The actuator being coupled to the shaft to extend the shaft from the handpiece. The curved shape of the shaft naturally changes the angle of the tissue engager relative to the handpiece as the shaft is extended longitudinally from the handpiece. The shaft changes the angle of the tissue engager relative to the handpiece by at least 45 degrees (to follow the curvature of the canal) when the shaft is extended from the handpiece.

The shaft may also be flexible and is deformed during use to provide a spring load on the tissue engager. In this manner, the shaft is resilient in the advancing direction so that the shaft develops a spring load in the advancing direction. Likewise, the shaft is also resilient in a direction perpendicular to the advancing direction (and lying in the plane of curvature). The resilient nature of the shaft as it relates to this direction causes a light spring load to develop in a radially outward direction relative to the axis of the eye (or the round shape of the canal). Thus, the shaft may be capable of developing a spring load which has a component in the advancing direction and a component in the radially outward direction. In this manner, the shaft is shaped to apply a radially outward force on the tissue (specifically a wall of the canal) when the tissue engager is moved through the trabecular meshwork.

The shaft effectively has a variable stiffness by changing a length of the shaft extending from the handpiece. The user may "dial in" the desired stiffness by extending or retracting the shaft and then manipulate the handle to move the tissue engager with the fixed stiffness and fixed length of shaft extending from the handle. The variable stiffness of the shaft may change by at least at factor of 10 when moving between a first working position and a second working position. The first and second working positions represent different lengths of the shaft extending from the introducer tube. The shaft may be capable of providing a stiffness in the advancing direction and/or the radial direction (which is orthogonal to the advancing direction) of less than 20 N/mm. The radial direction is a direction perpendicular to the advancing direction and lying in the plane of curvature. Forces exerted by the shaft in this direction (radially outward) tends to press the main body against the eye when moving the tissue engager to displace the tissue.

The tissue engager has a tissue engaging surface with a height measured perpendicular to an advancing direction which may be at least 300 microns or may be in a range of 550-1200 microns or even 800 to 1200 microns. The tissue engager and tissue engaging surface also have a width measured perpendicular to the advancing direction and to a radial direction in use which may be at least 300 microns or in a range of 300 to 700 microns.

The tissue engager may quickly gain a steep angle to gather, compress and push the tissue in the advancing direction. Many prior art devices use a relatively long angled ramped which tends to stretch and lift the tissue over the ramp. Such ramps may tend to stretch the tissue between the lateral sides and apply an upward force which may increase the likelihood that the tissue separates along a single separation line between the lateral sides rather than tearing along two lateral sides to remove tissue as described herein. The devices of the present invention may have a relatively small height H when the tissue engager begins to form a relatively steep angle to gather, compress and subsequently tear the tissue along the lateral sides. To this end, the main body extends proximally from the guide member and has a height which increases in proximal direction. When the increasing height reaches 0.014 inch the tissue engager increases to an angle of 60 degrees relative to the advancing direction within a distance D measured in the advancing direction of 0.035 inch. An alternative range is when the height reaches 0.012 inch that the angle reaches 80 degrees within 0.030 inch or when the height reaches 0.010 inch and the angle reaches 90 degrees within 0.025 inch. Stated another way, the height may be no more than 0.035 inch when the tissue engager 10 forms an angle of 80 degrees with the advancing direction AD or no more than 0.027 when the tissue engager 10 forms an angle of 90 degrees with the advancing direction.

The width of the tissue engager 10 may be somewhat moderate in the area where the tissue is gathered. The width may be 0.010 to 0.0030 inch when the tissue engager 10 increases to an angle of 80 degrees relative to the advancing direction or may be 0.012 to 0.0025 inch when the tissue engager 10 increases to an angle of 90 degrees relative to the advancing direction.

The device may also include a cutting element coupled to the tissue engager. The cutting element may be oriented to form a cut which is oriented radially outward relative to the central axis of the eye. The cutting element may be within 60 degrees, or even 30 degrees, or even 15 degrees, of the radially outward direction defined by the circular shape of the eye.

The cutting element is capable of forming a continuous cut in the wall of Schlemm's canal of at least 45 or even at least 90 degrees due to the nature of the shaft as described herein. Of course, smaller cuts (less angular extent) may be formed without departing from the scope of the invention.

The cutting element extends outwardly from the bottom surface of the tissue engager which slides against the canal wall in use. As such, the shaft also provides a light spring load in this direction to stabilize the cutting element. The circumferentially oriented cut in the wall may increase an effective size of Schlemm's canal by increasing the enclosed volume. The cutting element is also positioned so that the circumferential slit forms a channel which provides fluid communication at the fluid outflow side in the wall of Schlemm's canal formed by the sclera. The circumferential slit also increases the effective surface area available for fluid transfer and shortens the fluid path which is essentially circumferentially outward.

In use, the device is introduced into the anterior chamber of the eye in any suitable manner such as an ab interno approach. The tissue engager may be free of cutting or ablating elements so that the tissue is parted by trabeculorhexis in some embodiments while the cutting element may be used in conjunction with trabeculorhexis or independently. The tissue engager is moved to part tissue by trabeculorhexis and may not include cutting or ablating elements. The tissue engager displaces the tissue so that the tissue displaced by the tissue engager tears free from native tissue due to the displacement. Furthermore, no implantable structure is coupled to the handpiece or otherwise provided or deployed. Of course, an implantable may be incorporated without departing from the invention.

A suction lumen may be coupled to the handpiece for suctioning the tissue displaced by the tissue engager into the suction lumen. The introducer tube may form part of the suction lumen and the shaft may be retracted to clear some or all of the suction lumen. The device may also include a part-off mechanism to separate dislodged tissue strip from native tissue still attached to the eye. The part-off mechanism may be a loop with the tissue strip extending through the loop as the tissue engager is advanced.

These and other aspects of the present invention will become apparent from the following description of the preferred embodiments, drawings and claims.

BRIEF DESCRIPTION OF THE DRAWINGS

FIG. 13 shows another device for removing tissue from an eye.

FIG. 14 is an end view of the device of FIG. 13.

FIG. 15A shows another device having a shaft and a tissue engager which are integrally formed with a shaped wire.

FIG. 15B shows the distal end of the shaft and tissue engager of FIG. 15A.

FIG. 15C shows another view of the distal end of the shaft and tissue engager of FIG. 15A.

DESCRIPTION OF THE PREFERRED EMBODIMENTS

Referring to FIGS. 1-5, a device 2 for disrupting the inner canal wall is shown. In one aspect, the device 2 disrupts the canal wall by blunt trabeculorhexis. The trabeculorhexis bluntly engages and tears and/or shears the tissue or may accomplish a disinsertion of the trabecular meshwork from its attachment to the sclera and surrounding gonio anatomy without cutting. The device 2 has a tissue engager 10 mounted to a shaft 6. The tissue engager 10 is a non-cutting elongated blunt probe that engages the trabecular meshwork as it is moved through the canal and slides along an inner wall (or along an outer wall) of the Schlemm's canal. The device 2 includes a main body 12 which has the tissue engager 10 which may be a blunt tissue disruptor that spans the trabecular meshwork to form a continuous non-cutting trabeculorhexis. The device 2 stretches and tears the trabecular meshwork fibers as it follows the contour of the Schlemm's canal and may disinsert some of the tissue at the origin.

Figure 5:
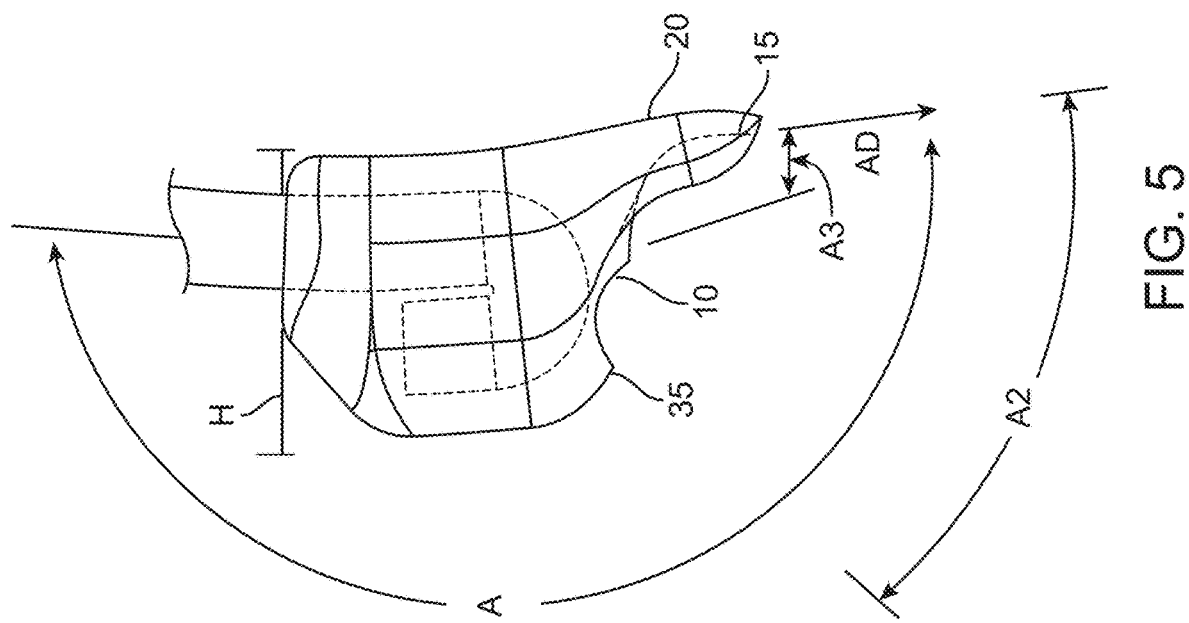
FIG. 5 shows another view of the tissue engager of FIG. 4.
Figure 4:
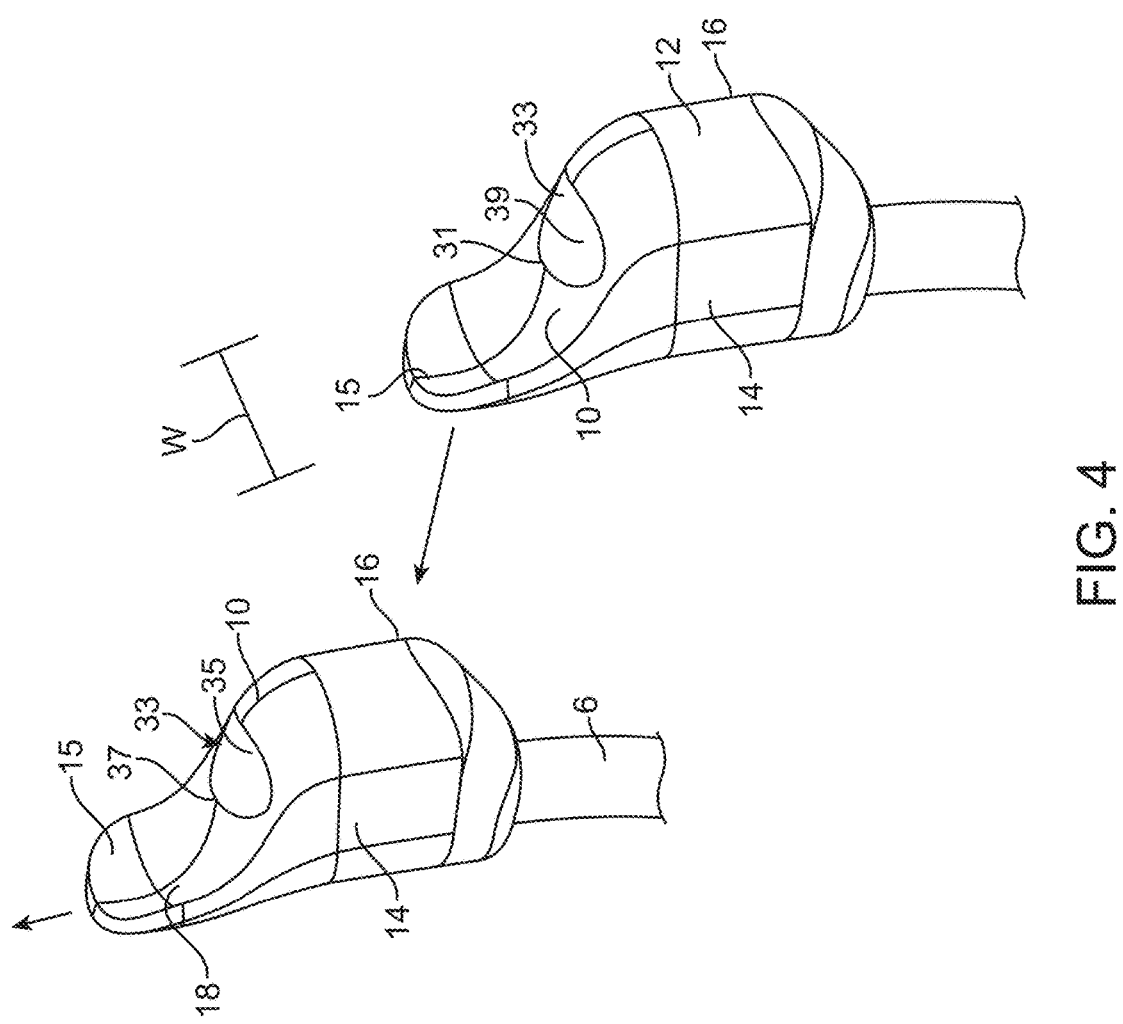
FIG. 4 shows a tissue engager mounted to a shaft.

Referring to FIGS. 4-5, the device 2 has a guide member 15 extending from the main body 12 which serves as a probing canal engagement front end which is blunt and non-incisional. The main body 12 has a first sidewall 14 on one side and a second sidewall 16 on an opposing lateral side. The tissue engager 10 is introduced into an anterior chamber of an eye and the guide member 15 is positioned adjacent a wall of Schlemm's canal (which may be an outer wall to leave Schlemm's canal intact or an inner wall when the guide member 15 is positioned within Schlemm's canal to remove part of Schlemm's canal). The tissue engager 10 is then moved by manipulating the shaft to advance the guide member in an advancing direction AD along the wall of Schlemm's canal and remove parts of the trabecular meshwork. The tissue engager 10 may be a blunt, non-incisional probe which is configured to engage the trabecular meshwork tissue ab-interno and bluntly tear or disinsert the trabecular meshwork tissue. The tissue engager 10 may strip an internal wall of the Schlemm's canal in use when the guide member is advanced within the canal. The guide member 15 extends distally from the main body 12 by a distance of 300 to 5000 microns although the guide member 15 may be shorter or longer without departing from numerous aspects of the present invention.

The shaft 6 extends proximally from the main body 12 (from the tissue engager 10) and may have a curved portion 11 which forms a semi-circle with a contour similar to the limbus architecture of the eye, (or can assume a curved memory shape/contour) which approximates a circle with a diameter of about 12 mm. The diameter of the arc span of the flexible shaft 6 may have a memory shape slightly exceeding the diameter of the average eye limbus which would enable a slight radially outward force due to the shape of the shaft 6 as it travels alongside the canal—allowing the firm outside scleral wall to further guide the device and minimizing pressure on the more fragile inner trabecular wall. The curved portion 11 may extend for an angle of greater than 135 degrees, and may be 160 to 200 degrees and may have a radius of curvature of 5.0 to 9.0 mm. A central plane CP is defined as a plane on which the advancing direction AD lies and which includes the shaft 6 at the connection of the shaft 6 to the tissue engager 10. The central plane CP may also be defined as the plane on which the advancing direction AD lies and which is positioned on a centerline of the tissue engager 10 when viewed along the advancing direction AD. The central plane CP may also be simply defined as the plane containing the circular shape of the Schlemm's canal. The shaft 6 can be a flexible memory shaped material as needed to substantially conform to the contour of the eye. The curved portion 11 also defines the plane of curvature in use. The shaft 6 has a curved shape which lies in the plane of curvature in use which is aligned with the plane on which the circular Schlemm's canal lies.

Referring again to FIGS. 1-3, the device 2 includes a handpiece 13 with the shaft 6 being coupled to the handpiece 13 and being manipulated with an actuator 25 which translates the shaft 6 forward and back to extend and retract the shaft 6 from the handpiece 13. When the shaft 6 is extended from the handpiece 13 in use the curved portion 11 of the shaft 6 naturally changes the angle of the tissue engager 10 (and the orientation of the longitudinal axis of the shaft 6 at the distal end) relative to the handpiece by at least 45 degrees and may be even up to 180 degrees. The curved portion of the shaft naturally changes the angle of the tissue engager 10 relative to the handpiece as the shaft 6 is extended longitudinally from the handpiece.

The handpiece 13 may also include an introducer 17 (FIG. 2A and FIG. 2B) with the elongate shaft 6 extending through a lumen 19 in the introducer 17. The curved portion 11 of the shaft 6 is in a straightened and biased condition when contained within the lumen 19 of the introducer 17. The introducer 17 may have a curved tip 21 at a distal end 23 which is curved by 15-60 degrees to facilitate insertion of the device 2 into the trabecular meshwork and to direct the tissue engager 10 in the desired direction along Schlemm's canal. A distal end 27 of the lumen 19 is inserted into the trabecular meshwork while the tissue engager 10 is contained within the lumen 19. The curved tip 21 of the introducer 17 is curved by 15-60 degrees to facilitate smooth entry into (or onto the outer wall of) Schlemm's canal. The lumen 19 may also be coupled to a source of suction so that the tissue may be removed from the eye with the device 2. Alternatively, tissue may be removed with a separate suction device.

Figure 1B:
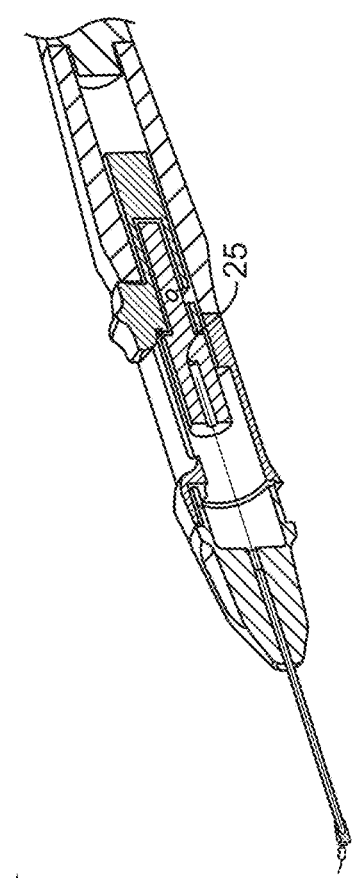
FIG. 1B is a cross-sectional view of the handpiece of FIG. 1A.
Figure 1D:
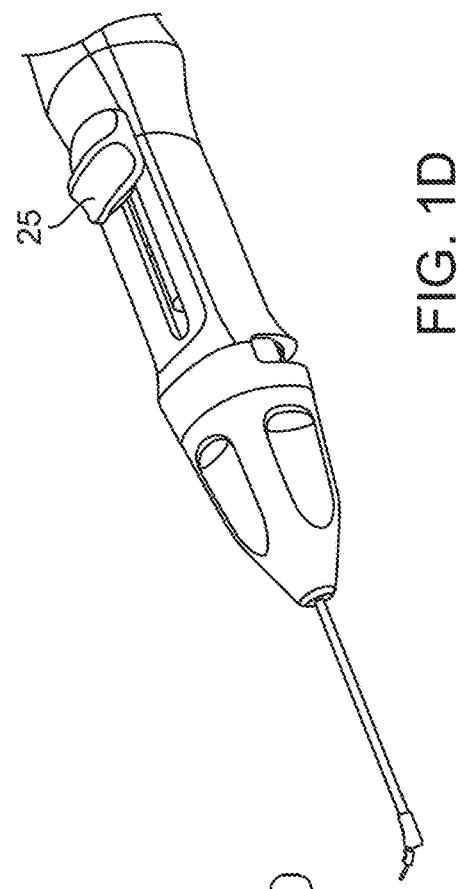
FIG. 1D is an enlarged view of the distal end of the device of FIG. 1A.
Figure 1A:
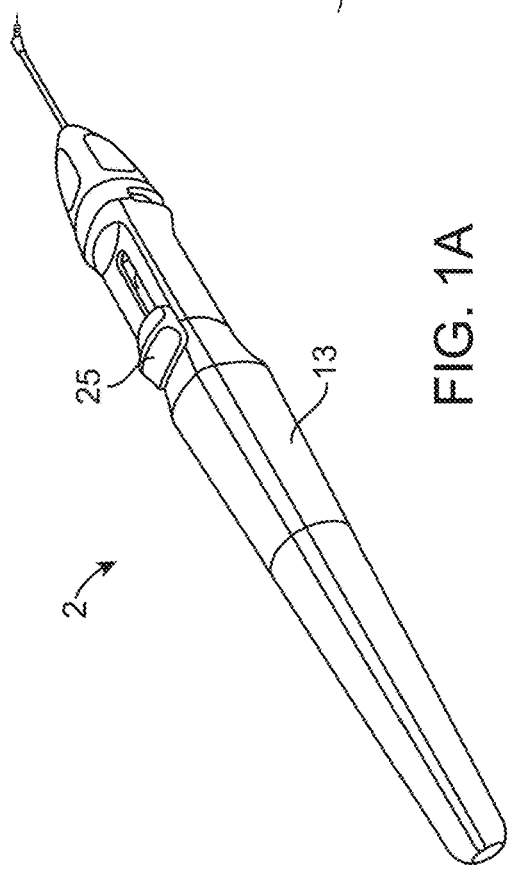
FIG. 1A shows a device for removing tissue from an eye having a handpiece with an actuator to manipulate a tissue engager.
Figure 1C:
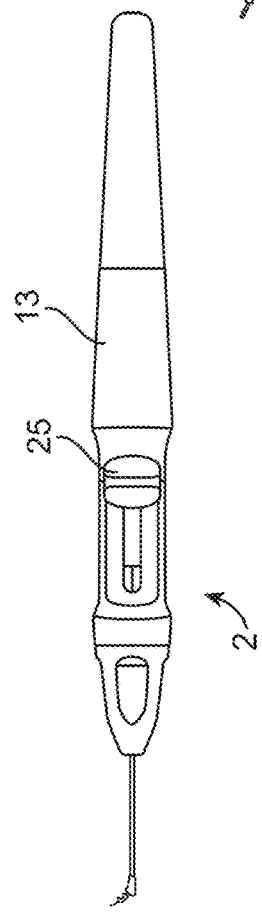
FIG. 1C is a top view of the handpiece of FIG. 1A.
Figure 2A:
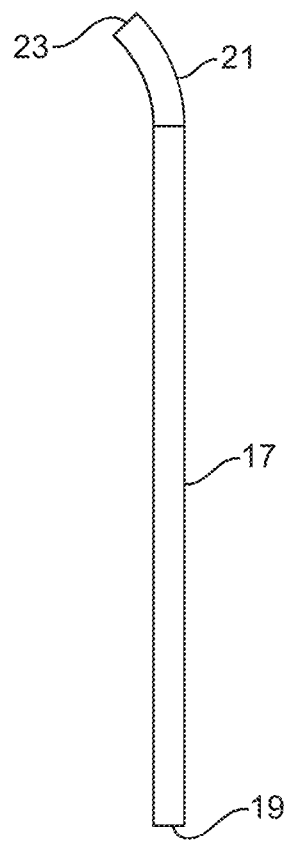
FIG. 2A shows an introducer tube which receives the shaft of the tissue engager.
Figure 2B:
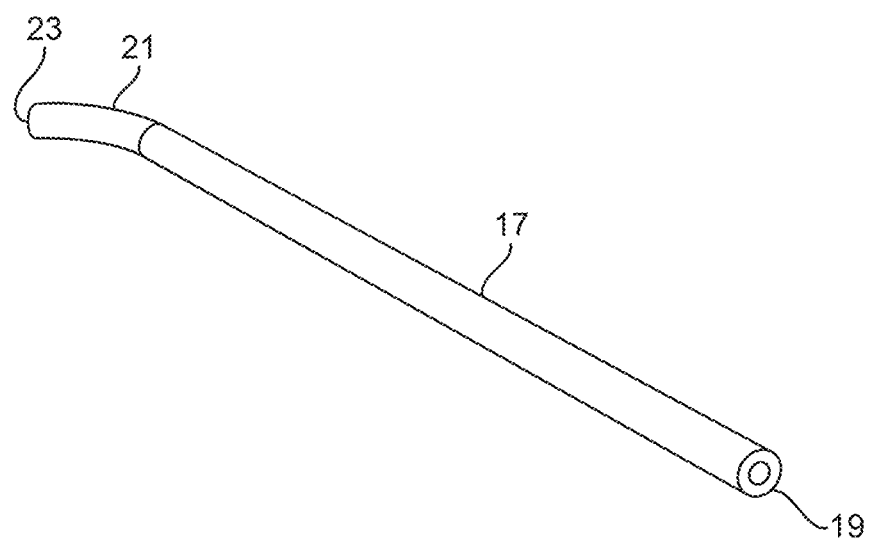
FIG. 2B is a perspective view of the introducer tube of FIG. 2A.
Figure 3A:
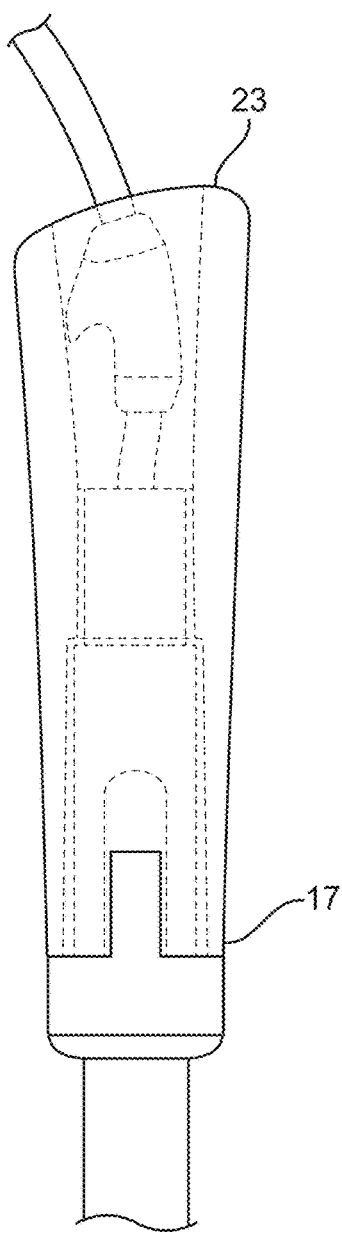
FIG. 3A shows an end of the introducer with the tissue engager contained within the lumen of the introducer.
Figure 3B:
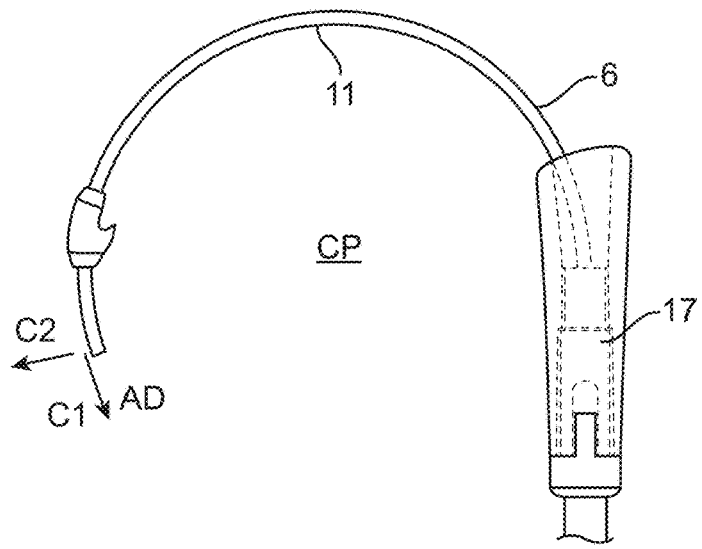
FIG. 3B shows another view of the end of the introducer with the curved shaft extended to advance the tissue engager.
Figure 3C:
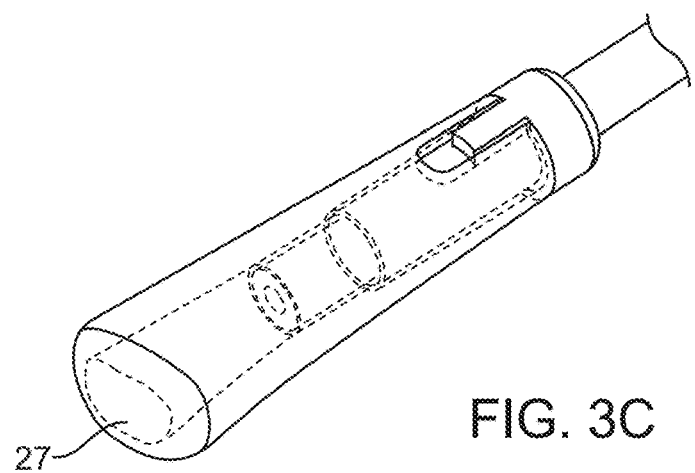
FIG. 3C shows an enlarged view of the distal end of the introducer.

Referring to FIG. 3B, the elongate shaft 6 may be flexible and resilient to provide a "soft" feel during use with the shaft 6 being elastically deflected and deformed in use. Specifically, the shaft 6 may be resilient relative to forces exerted against the tissue engager 10 in the advancing direction AD. The shaft 6 may be made of a metal and may be a superelastic material such as nitinol which provides a wide range of elastic response. For example, the shaft may be 0.15 mm diameter nitinol wire and may be 0.10 to 0.25 mm. In this manner, the shaft 6 develops a light spring load in the advancing direction AD as it is advanced. The curved portion 11 of the shaft 6 also provides a resilient response in a direction perpendicular to the advancing direction AD and lying in the plane of curvature. Thus, the shaft 6 may develop a spring load with a component C1 in the advancing direction and a component C2 in a radially outward direction relative to the axis of the eye. In this manner, the radially outward force causes the tissue engager 10 to slide against the sclera (or outer wall of Schlemm's canal) to stabilize the tissue engager 10. Stated another way, as the tissue engager 10 is moved through the trabecular tissue, the curved shaft 6 is shaped to apply a radially outward force on the tissue relative to the axis of the eye. The resilient nature of the shaft 6 also prevents excessive forces from being applied to the eye inadvertently. The soft, spring-loaded nature of the shaft may also limit or prevent accidental application of excessive force or displacement. The curved portion 11 of the shaft 6 may extend for an angle of greater than 180 degrees and may be 240 degrees or more. The curved portion 11 may have a radius of curvature of about 7.5 mm.

As used herein, when referring to the stiffness, resiliency or spring constant of the shaft 6 requires the shaft 6 to have (or be positioned or otherwise configured) to be operable when moving the tissue engager to displace the tissue to be removed. The shaft 6 may have a stiffness in the advancing direction of less than 20 N/mm, less than 10 N/mm or even less than 5 N/mm, when the tissue engager is moved to displace the tissue. The shaft 6 may also have a stiffness in a direction perpendicular to the advancing direction and lying the plane of curvature of less than 20 N/mm, less than 10 N/mm or even less than 5 N/mm, which presses the main body against the eye when moving the tissue engager to displace the tissue. When the guide member is positioned in Schlemm's canal the perpendicular force presses the main body (and guide member) against the sclera. The shaft 6 may have the desired stiffness characteristics while the shaft 6 is able to change the angle of the tissue engager 10 by at least 45 degrees and may be at least 90 degrees (by extension or retraction of the shaft). The angle of the shaft 6 is changed by simply extending the shaft 6 from the introducer 17. The shaft 6 extends from the tissue engager 10 at an angle A of greater than 90 degrees, or even greater than 135 degrees, and may be 160 to 200 degrees or even 160 to 240 degrees, relative to the advancing direction AD. An advantage of the shaft 6 is that complex movements of the handpiece are reduced compared to devices having rigid shafts which require the shaft angle to be changed as the device is advanced through the canal. Non-flexible (rigid) shafts are limited to partial pivot angulation at the site of ab-interno entry into the anterior chamber (between 10-120 degrees only). Instead, the flexible shaft of the present invention may be made of elastic or superelastic alloys or polymers which provide sufficient flexibility to access the entire internal circumference of the anterior chamber and the gonio anatomy. Such movements with a rigid shaft can be challenging given the limited degrees of freedom and movement for devices introduced into the eye. The present invention reduces and can even eliminate the need to change the angle of the shaft/handpiece when disrupting the canal. Although the present invention describes trabeculorhexis rather than cutting, numerous aspects of the present invention may be practiced with a cutting element rather than one that rips/strips/tears the tissue. For example, all aspects of the shaft 6 may be practiced with the tissue engager 6 cutting tissue.

The shaft 6 also has a variable stiffness by simply changing a length of the shaft 6 extending from the handpiece 13 which may provide obvious advantages when encountering differing tissue conditions and angles of approach. The variable stiffness of the shaft 6 may change by at least at factor of 10 when moving between a first working position and a second working position so that the first position with the smallest stiffness is at least 10 times smaller than the second position with the larger stiffness with both positions being operable to displace the tissue. The variable stiffness may be provided by simply retracting and extending the shaft 6 to change a length of the shaft 6 extending from the handpiece (specifically the introducer) and the first and second working positions may change the orientation of the distal end of the shaft by at least 45 degrees relative to the handpiece 13. The shaft 6 cross-section may be constant or may increase proximally to maintain a more consistent stiffness. For example, the stiffness may vary less than 30% for a curved portion which is extended and retracted to change the angle of the shaft 6 by at least 45 degrees.

The guide member 15 has an upper surface 18 and a lower surface 20 with the lower surface 20 positioned adjacent the wall of Schlemm's canal so that the guide member 15 slides against the sclera or outer wall of Schlemm's canal. The tissue engager 10 has a height H measured perpendicular to the advancing direction AD (and transverse to the wall of Schlemm's canal in an essentially radially inward direction relative to the circular shape of the canal) from the upper surface 18 to the lower surface 20 which is at least 150 microns and may be 500 to 1200 microns or even 500 to 800 microns although any suitable height may be used depending on the desired amount of trabecular meshwork to be stripped. The tissue engager 10 has a width W measured perpendicular to the advancing direction (and to the height H) of at least 300 microns or at least 400 microns and may be 300 to 700 microns, or 450-850 microns or even 500-700 microns.

The height H and width W of the tissue engager are intended to capture and gather the trabecular meshwork. In this manner, the gathered tissue is less likely to tear or rip between the first and second sidewalls 14, 16 compared to the tissue along the first and second sidewalls 14, 16. The lower surface 20 slides against a wall of Schlemm's canal or the sclera. The tissue may be gathered by the upper surface 18 with the upper surface 18 spaced apart from the lower surface 20 by 250 to 700 microns or 400 to 700 microns with alternative ranges for being 250 to 550 microns and may even be 250 to 450 microns at a center of the upper surface 18 with the center of the upper surface 18 being the furthest part of the upper surface 18 from the lower surface 20.

The tissue engager 10 has a tissue engaging surface 31 which may have a concave portion 33 when viewed perpendicular to the advancing direction. The concave portion 33 has an upper lip 35 and a lower lip 37 which may help gather and compress tissue together as the device 2 is advanced. The upper lip 35 may form an angle A2 of less than 90 degrees (and may be 30-70 degrees) with the advancing direction AD when viewed perpendicular to the advancing direction while the lower lip 37 may form an angle A3 of 0-30 degrees with the advancing direction AD when viewed perpendicular to the advancing direction AD. The concave portion 33 forms a recess 39 when viewed perpendicular to the advancing direction AD. The recess 39 has a depth of at least 50 microns measured perpendicular to a line extending between the upper lip 35 and the lower lip 37 of the recess 39. Stated another way, the recess 39 has a recess depth measured in the advancing direction of at least 100 microns, at least 200 microns or even 300-600 microns. The recess 39 has a recess height measured perpendicular to the advancing direction and parallel to the central plane of at least 200 microns and may be 300-600 microns. The recess 39 may also have a recess width measured perpendicular to the advancing direction AD and to the central plane CP of 300 to 700 microns and may be 400 to 600 microns.

The first sidewall 14 and the second sidewall 16 extend from the tissue engaging surface 31 on opposing lateral sides of the tissue engaging surface 31. The first sidewall 14 and the second sidewall 16 may have a height of at least 150 microns and may be 500 to 800 microns (measured perpendicular to the advancing direction AD) and a length of 200-500 microns (measured along the advancing direction AD). The first sidewall 14 and the second sidewall 16 may also form an angle with the central plane CP of less than 45 degrees and may even be less than 20 degrees. The first sidewall and the second sidewall extend from the tissue engaging surface 31 on opposing lateral sides of the tissue engaging surface 31.

The tissue engager 10 may gather tissue and displaces the tissue with a blunt non-lacerating engagement. As the tissue engager 10 moves the gathered tissue forward, tissue along the first and second sidewalls 14, 16 is sheared and/or torn without cutting or the need for a cutting element. Stated another way, the tissue engager 10 compresses and gathers tissue to bunch the tissue between the upper lip 35 and the lower lip 37 in a direction perpendicular to the advancing direction AD and lying in the central plane CP. The tissue engager 10 compresses and gathers tissue while the tissue is torn and sheared along the first and second sidewalls 14, 16 during displacement of the gathered tissue. The tissue engager 10 may be moved through the trabecular meshwork continuously along any angular extent such as 10-360 degrees or 30 to 120 degrees of the Schlemm's canal. The tissue engager 10 shears tissue along the first sidewall 14 and the second sidewall 16 due to displacement of tissue gathered by the tissue engager 10. Stated another way, the tissue engager 10 compresses and gathers tissue to bunch the tissue in a direction perpendicular to the advancing direction and lying in the central plane. Stated still another way, the tissue engager 10 compresses and gathers tissue while the tissue is torn along the first sidewall 14 and the second sidewall 16 due to displacement of tissue gathered by the tissue engager 10. The tissue engager 10 may also lack any piercing elements and may tear the tissue without cutting or ablating although numerous aspects may be practiced with the tissue engager 10 cutting tissue as mentioned above. The tissue engager 10 is a blunt, non-incisional probe and may displace the trabecular meshwork tissue to bluntly disinsert the trabecular meshwork tissue.

The tissue engager 10 may strip an internal wall of the Schlemm's canal when the guide member 15 is advanced through the canal or may leave the canal intact with the guide member 15 sliding on the outer wall of the canal. The tissue engager 10 has the tissue engaging surface 31 proximal to the guide member 15. The tissue engaging surface 31 may contact and displace tissue without cutting the tissue. The tissue engaging surface 31 has an orientation which is within 15 degrees, and may be within 10 degrees, of perpendicular to the advancing direction AD. The tissue engaging surface 31 may have a width W of at least 400 microns and may be 500-800 microns. The tissue engaging surface may have a height H of at least 300 microns, at least 400 microns, at least 500 microns or may be 550-1200 microns or even 800 to 1200 microns. The width W of the tissue engaging surface helps to gather an amount of tissue ahead of the tissue engaging surface. In this manner, the tissue is ripped/torn/sheared from the native tissue due to displacement of the tissue gathered ahead of the tissue engaging surface. Displacing tissue in this manner encourages the tissue to be torn on both lateral sides thereby releasing a strip of the trabecular meshwork. Thus, stated another way, the tissue engaging surface displaces an amount of tissue having a width of at least 300 microns and may be at least 400 microns.

Figure 6:
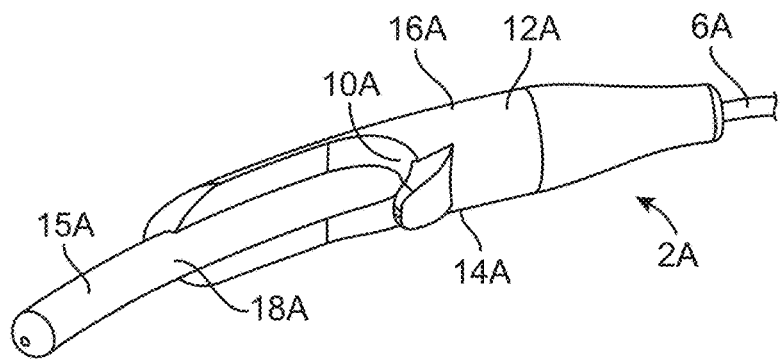
FIG. 6 shows another device for removing tissue from the eye.
Figure 7:
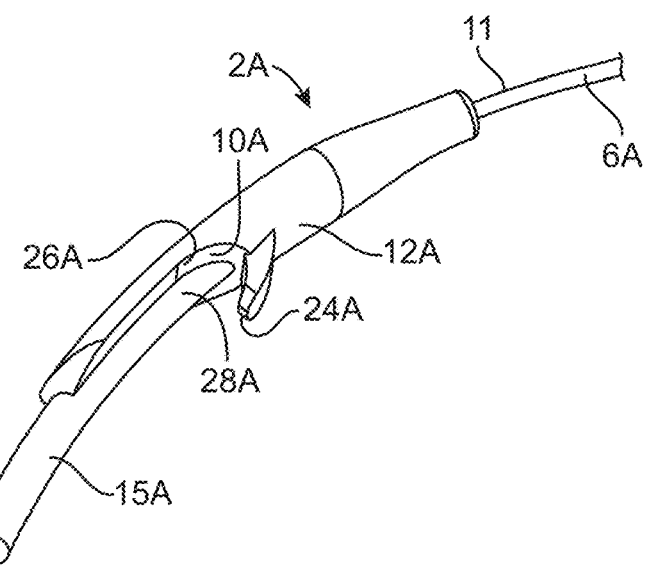
FIG. 7 is a side view of the device of FIG. 6.
Figure 8:
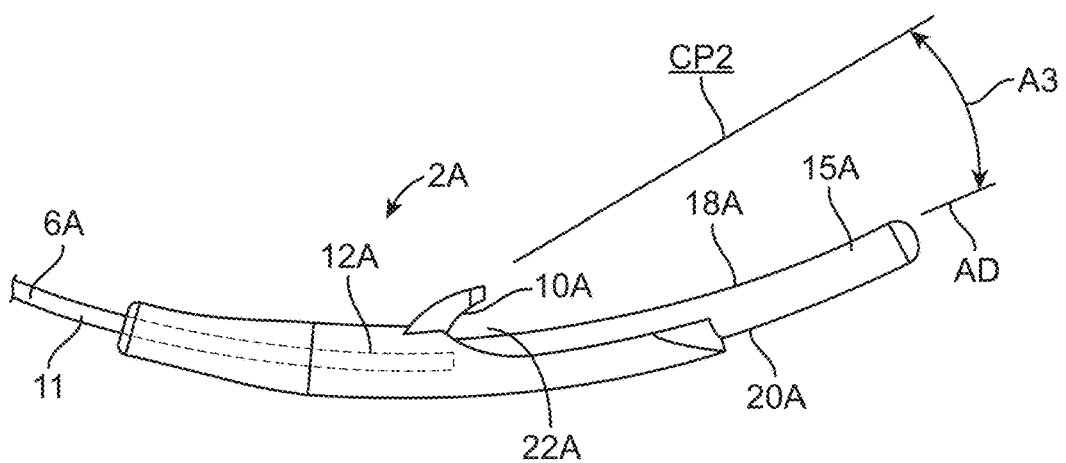
FIG. 8 is a top view of the device of FIG. 6.
Figure 10:
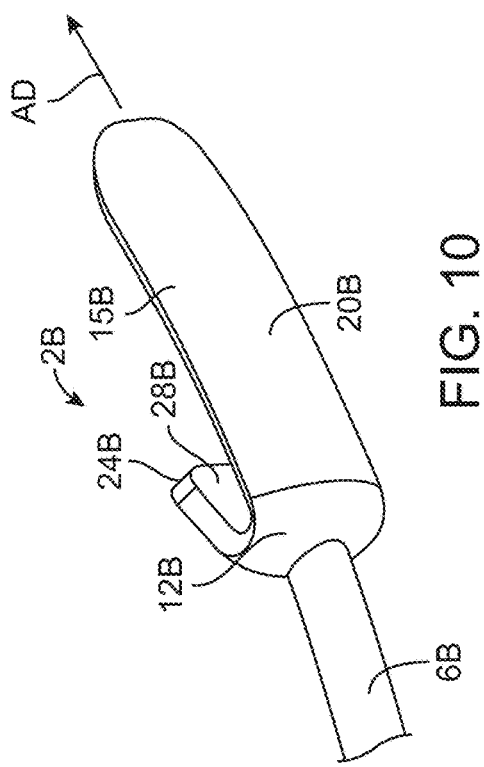
FIG. 10 shows the lower surface of the guide member of the device of FIG. 9.
Figure 12:
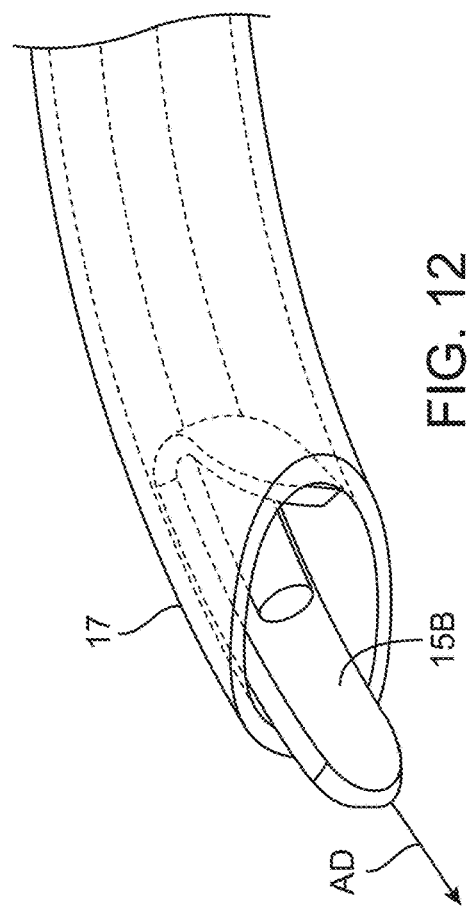
FIG. 12 shows the tissue engager of FIG. 9 with the guide member partially extending from the introducer.
Figure 9:
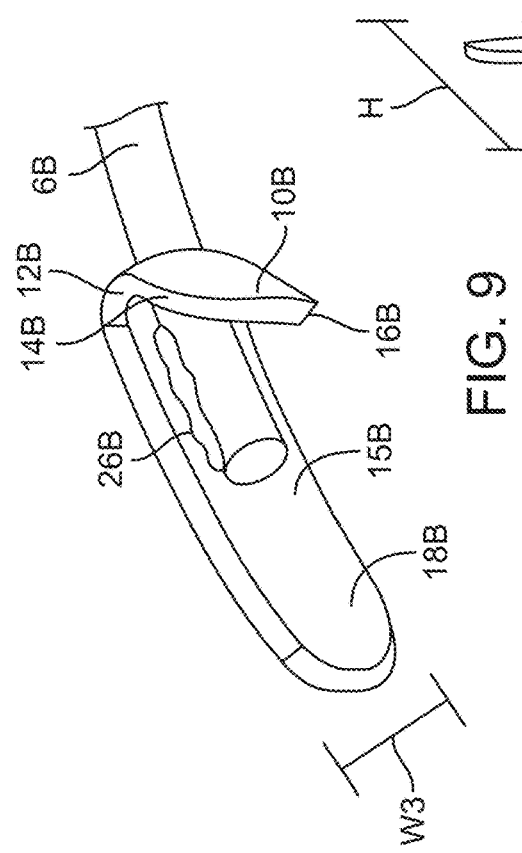
FIG. 9 shows another device for removing tissue from the eye.
Figure 11:
FIG. 11 is a side view of the tissue engager of FIG. 9 contained within the introducer.
Figure 16:
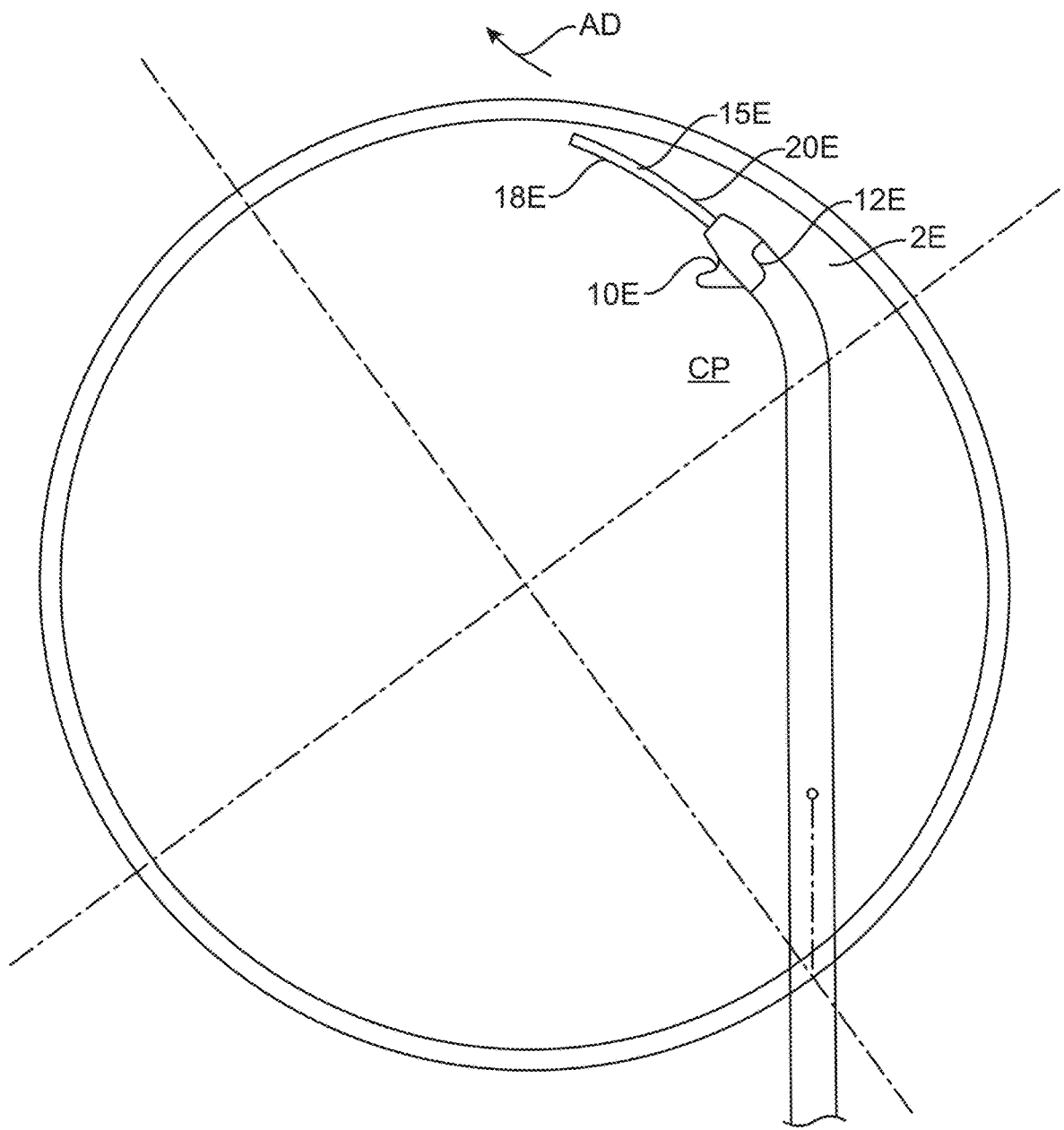
FIG. 16 shows another device for removing tissue from an eye.
Figure 17:
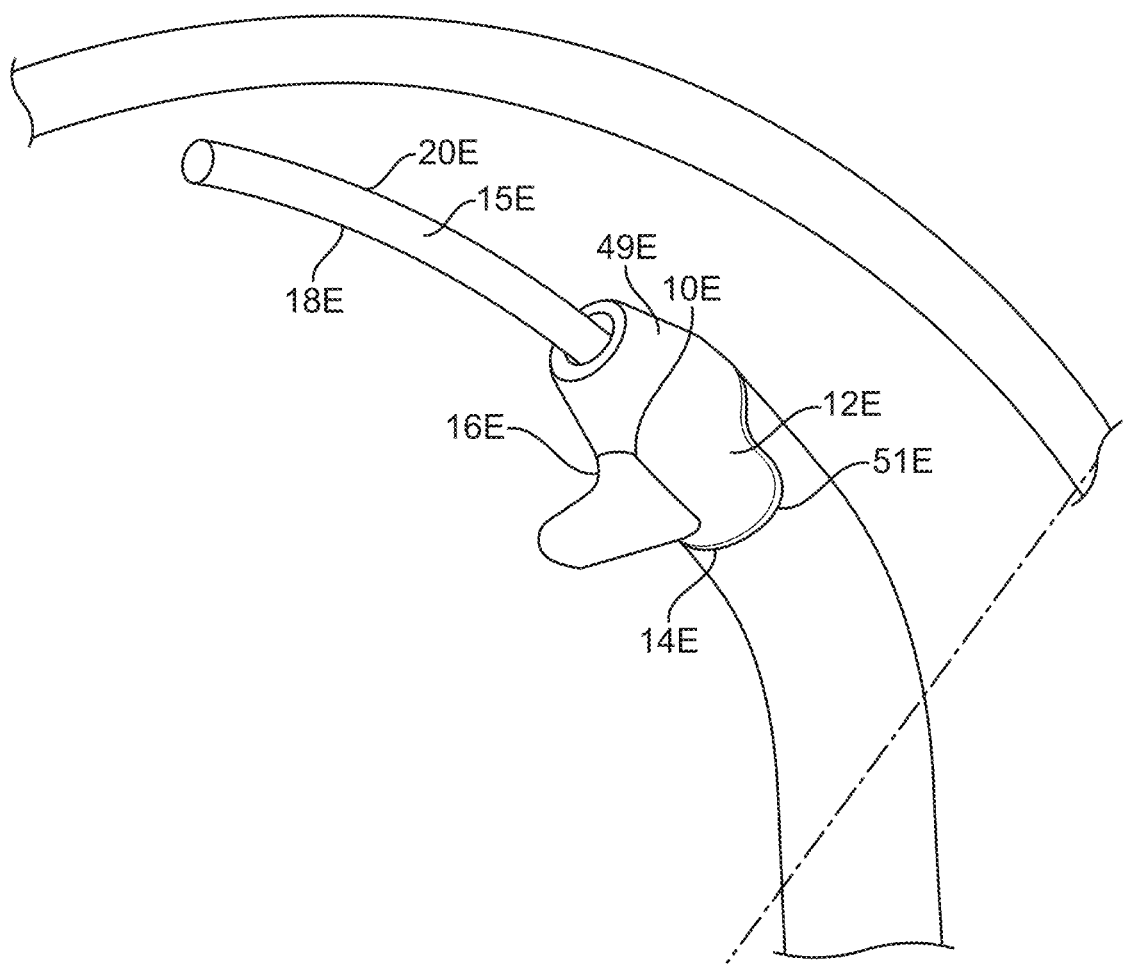
FIG. 17 shows the distal end of the device of FIG. 16.
Figure 18:
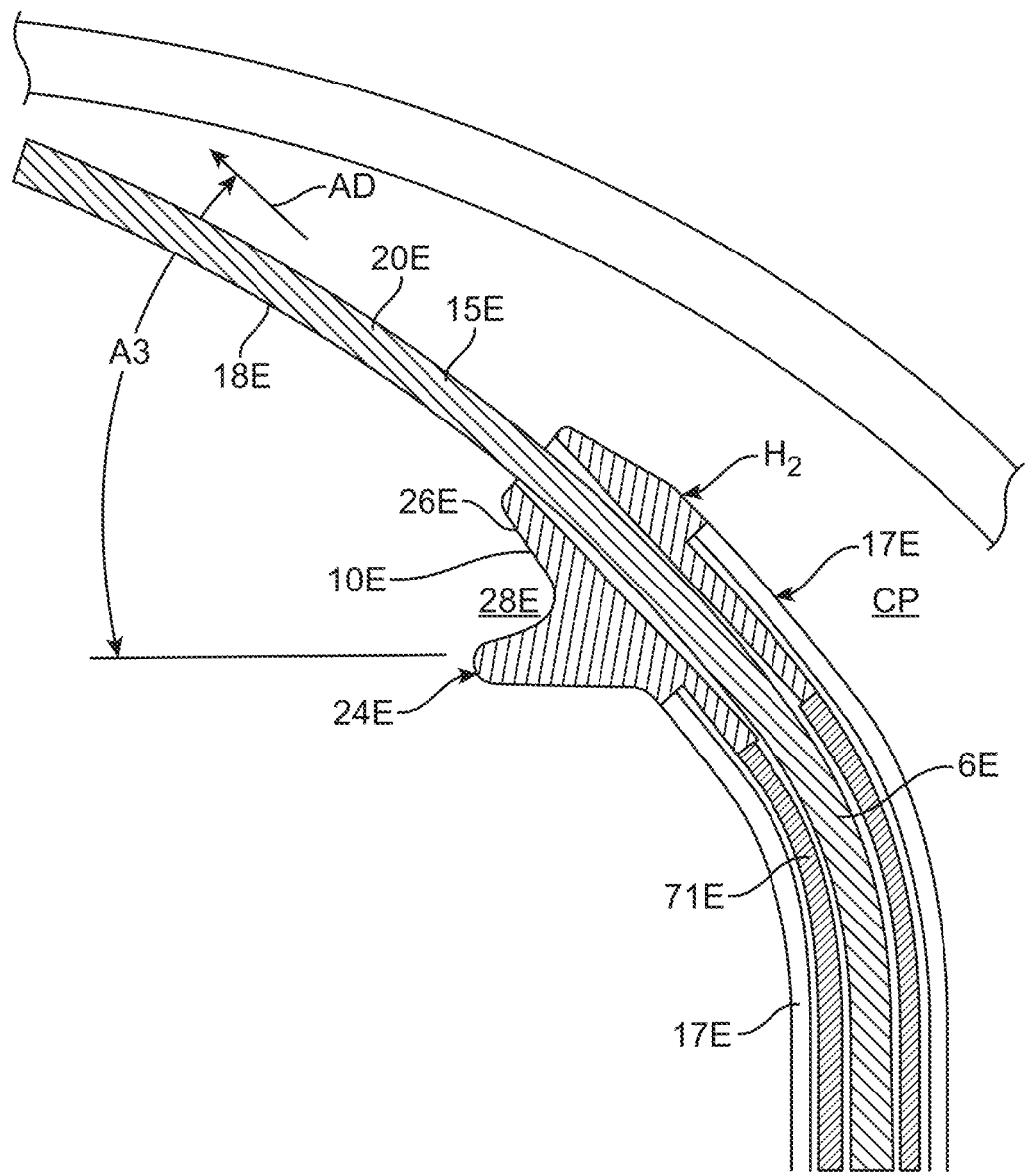
FIG. 18 shows a cross-sectional view of the distal end.
Figure 19:
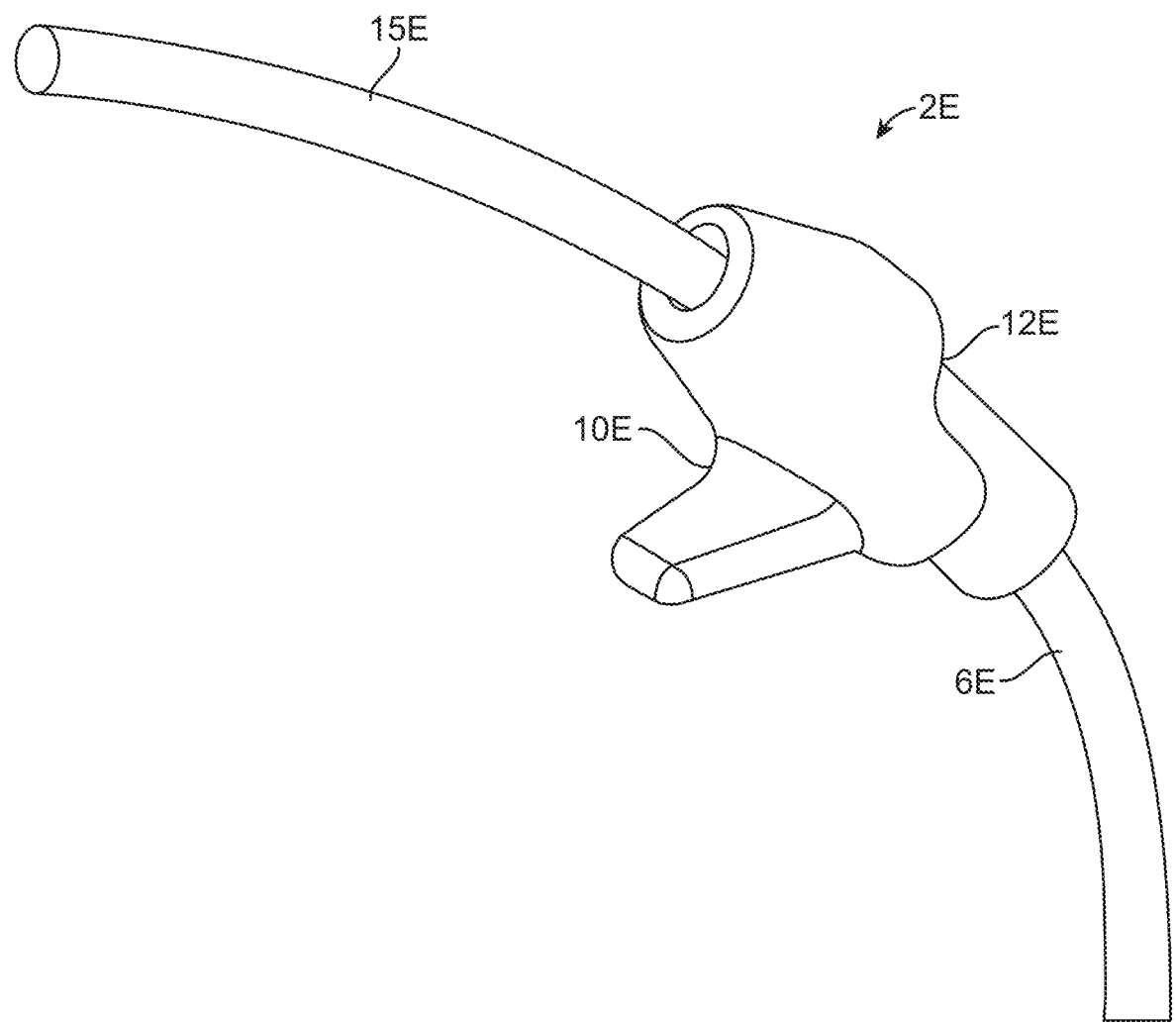
FIG. 19 shows the distal end with the shaft advanced from the introducer.
Figure 20:
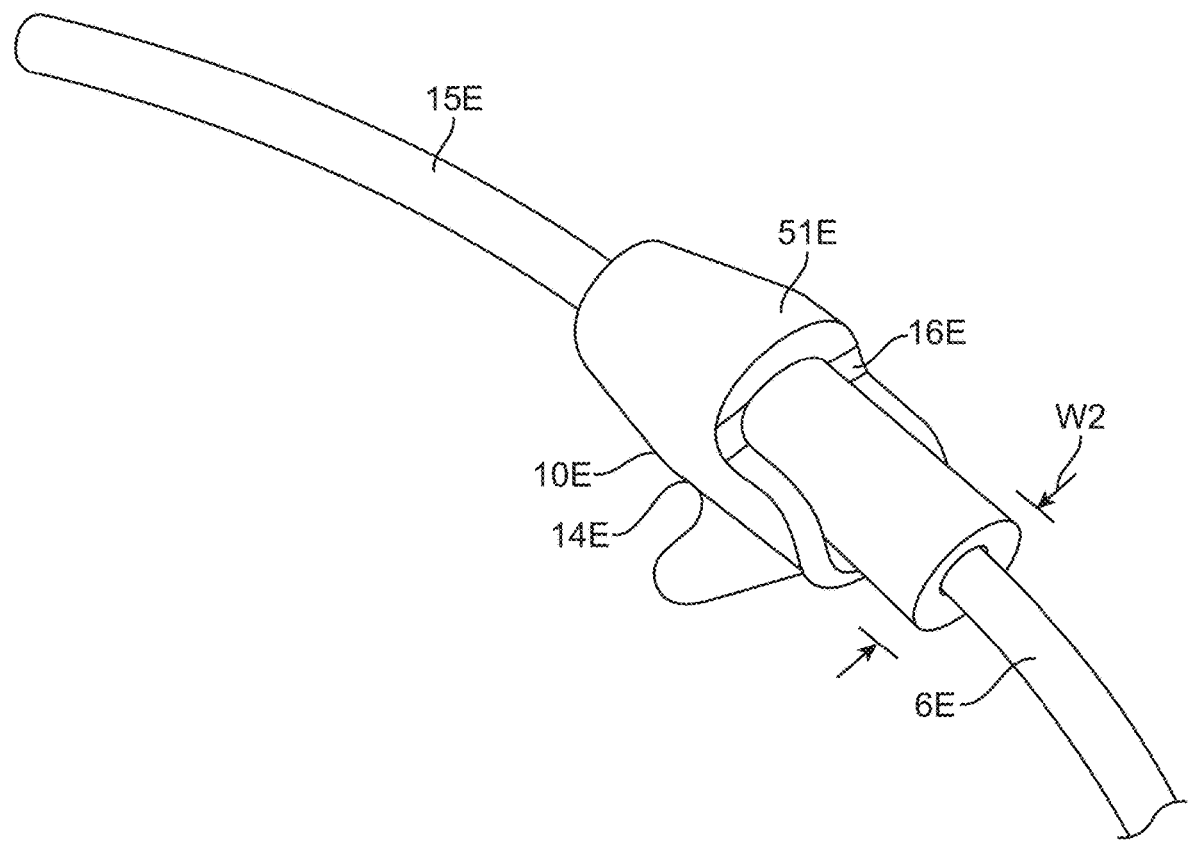
FIG. 20 is another view of the distal end.

Referring to FIG. 6-8, another device 2A for removing tissue from the eye is shown wherein the same or similar reference numbers refer to the same or similar structure. The device 2A has a tissue engager 10A mounted to a shaft 6A. The shaft 6A may have any of the properties of the shaft 6 described herein and the shaft 6A is mounted to the handpiece 13 (FIG. 1A) in the same manner and use as the shaft 6 and all such uses, features and properties are incorporated here. The device 2A also has a non-cutting non-ablative tissue engager 10A that engages and displaces the trabecular meshwork. The tissue engager 10A (which is formed by a main body 12A) gathers tissue (trabecular meshwork) so that the tissue stretches and tears along a first sidewall 14A and a second sidewall 16A as it follows the contour of the Schlemm's canal. The shaft 6A may also be made of any suitable material and may be a metal, including a superelastic material such as nitinol.

The device 2A has a guide member 15A to guide the device 2A along Schlemm's canal. The main body 12A has the first sidewall 14A and the second sidewall 16A on opposing lateral sides of the main body 12A. The guide member 15A may extend distally from the main body 12A by a distance of 30-500 microns although the guide member 16A may be shorter or longer without departing from numerous aspects of the present invention. The shaft 6A extends proximally from the tissue engager 10A. A central plane CP2 is defined as a plane on which the advancing direction AD lies and which includes the shaft 6A at the connection of the shaft 6A to the main body 12A (and to the tissue engager 10A). The central plane CP2 may also be defined as the plane on which the advancing direction AD lies and the curved portion 11 of the shaft 6A. The central plane CP2 also defines the plane on which Schlemm's canal lies.

The guide member 15A has an upper surface 18A and a lower surface 20A with the lower surface 20A sliding against a wall of Schlemm's canal in use. The tissue engager 10A has a height H measured perpendicular to the advancing direction AD which is less than 600 microns and may be 50-500 microns. The tissue engager 10A also has a width W (measured perpendicular to the advancing direction) which may be 50 to 500 microns. The tissue engager 10A may also have a tissue engaging surface with a concave portion 22A when viewed perpendicular to the advancing direction AD.

The concave portion 22A has an upper lip 24A and a lower lip 26A which helps to gather and compress tissue as the device 2A is advanced. The upper lip 24A may form an angle A3 of less than 90 degrees, alternatively an angle of 30-70 degrees, with the advancing direction AD when viewed perpendicular to the advancing direction AD. The concave portion 22A may form a recess 28A (when viewed perpendicular to the advancing direction) with the recess 28A having a depth of at least 50 microns measured perpendicular to a line extending between the upper lip and lower lip.

The first sidewall 14A and the second sidewall 16A extend from the tissue engaging surface on opposing lateral sides of the tissue engaging surface. The first sidewall 14A and the second sidewall 16A may have a height of 500 to 800 microns (measured perpendicular to the advancing direction AD) and a length of 180 to 220 microns (measured along the advancing direction AD).

Referring to FIGS. 9-12, another device 2B for removing tissue from the eye is shown wherein the same or similar reference numbers refer to the same or similar structure. The device 2B has a tissue engager 10B mounted to an elongate shaft 6B to form the non-cutting blunt tissue engager 10B. The tissue engager 10B (which is formed by a main body 12B) stretches and tears the trabecular meshwork fibers as described herein. The shaft 6B may also be made of a metal such as a superelastic material (nitinol).

The device 2B has a guide member 15B which guides the device 2B along Schlemm's canal. The guide member 15B may be a piece of formed sheet metal. The main body 12B has a first sidewall 14B and a second sidewall 16B on opposing lateral sides of the main body 12B. The guide member 15B may extend distally from the main body 12B by a distance of 30-500 microns. A central plane CP3 is defined as a plane on which the advancing direction AD lies and which includes the shaft 6B at a connection of the shaft 6B to the tissue engager 10B. The central plane CP3 may also be defined as the plane on which the advancing direction AD lies and which is positioned on a centerline of the tissue engager 10B when viewed along the advancing direction AD. The shaft 6B may be a flexible memory shaped material as needed to follow the contour of the eye.

The guide member 15B has an upper surface 18B and a lower surface 20B with the lower surface 20B sliding against a wall of Schlemm's canal during use. The lower surface 20B may be laser etched, chemical etched or ground to provide a desired texture. The tissue engager 10B has a height H measured perpendicular to the advancing direction AD and a width W3 (measured perpendicular to the advancing direction) which may have the dimension ranges for any of the other devices described herein and all such dimensions are incorporated here.

The tissue engager 10B may also have a tissue engaging surface with a concave portion 22B when viewed perpendicular to the advancing direction AD. The concave portion 22B has an upper lip 24B and a lower lip 26B which helps to gather and compress tissue as the device 2B is advanced. The gathered tissue is displaced and the gathered/displaced tissue tears/shears/rips the tissue from the native tissue. The upper lip 24B may form an angle of less than 90 degrees, alternatively an angle of 30-70 degrees, with the advancing direction AD when viewed perpendicular to the advancing direction AD3. The concave portion 22B may form a recess 28B (when viewed perpendicular to the advancing direction) with the recess 28B having a depth of at least 50 microns measured perpendicular to a line extending between the upper lip 24B and the lower lip 26B. The recess 28B may be partially defined by the elongate shaft 6B but may, of course, also be formed independent of the shaft 6B.

The first sidewall 14B and the second sidewall 16B extend from the tissue engaging surface on opposing lateral sides of the tissue engaging surface. The first sidewall 14B and the second sidewall 16B may have a height, width, orientation and size ranges of any of the other embodiments described herein which are incorporated here.

Referring to FIGS. 13 and 14, still another device 2C for removing tissue from the eye is shown wherein the same or similar reference numbers refer to the same or similar structure. The device 2C has a tissue engager 10C mounted to an elongate shaft 6C to form a non-cutting elongated blunt probe.

The tissue engager 10C (which is formed by a main body 12C) stretches and tears the trabecular meshwork fibers as described herein. The shaft 6C may be a nitinol wire or any other suitable material. The tissue engager 10C may be a plastic extrusion bonded which is bonded or formed with the shaft 6C. The main body 12C has a first sidewall 14C and a second sidewall 16C on opposing lateral sides of the main body 12C where the trabecular meshwork is torn. As such, the gathered tissue displaced by the tissue engager 10C has been substantially freed from the native tissue. The tissue engager 10C has a height measured perpendicular to the advancing direction which may be at least 150 microns (and may be 500 to 800 microns). The tissue engager 10C has a width W measured perpendicular to the advancing direction of at least 400 microns and may be 450-850 microns or even 500-700 microns.

The elongate shaft 6C extends beyond a distal end of a main body 12C to form a guide member 15C. Stated another way, the elongate shaft 6C extends distally from tissue engager 10C to form at least part of the guide member 15C so that the elongate shaft 6C defines a distal end of the guide member 15C. The guide member 15C is formed by the shaft 6C and may extend distally from the main body 12C by a distance of 30-500 microns. The guide member 15C has an upper surface 18C and a lower surface 20C with the lower surface 20C sliding against a wall of Schlemm's canal during use. The upper surface 18C of the guide member 15C may have a convex surface with a radius of curvature of 100 to 350 microns, or even 200 to 300 microns, and may be defined at least partially (or entirely) by the elongate shaft 6C. The upper surface 18C may have a radius of curvature less than a radius of curvature of the lower surface 20C. The lower surface 20C may be rounded with a radius of curvature 400 to 750 microns when viewed along the advancing direction.

The elongate shaft 6C may also have a non-circular cross-sectional shape with a minor axis 51 and a major axis 53. The major axis being within 30 degrees, and may be within 15 degrees, of perpendicular to the central plane. The major axis may be at least 20% larger than the minor axis. The minor axis may be less than 250 microns while the major axis may be larger than 250 microns. The shaft 6C may be interchanged with any of the other shafts described herein and vice versa and all such features, such as the non-circular cross-section of shaft 6C, may be used with any of the other shafts described herein including all aspects of shaft 6 such as the spring loads developed.

The first sidewall 14C and the second sidewall 16C extend from the tissue engaging surface on opposing lateral sides of the tissue engaging surface. The first sidewall 14C and the second sidewall 16B may have a height of 500 to 800 microns (measured perpendicular to the advancing direction AD) and a length of less than 100 microns (measured along the advancing direction AD). The first sidewall 14C and the second sidewall 16C may also form an angle with the central plane CP4 of less than 45 degrees and may even be less than 20 degrees. The central plane CP4 is defined as a plane on which the advancing direction AD lies and which includes the shaft 6C at a connection of the shaft 6C to the tissue engager 10C. The central plane CP4 may also be defined as the plane on which the advancing direction AD lies and which is positioned on a centerline of the tissue engager 10C when viewed along the advancing direction AD. Yet another definition is the plane on which the tissue engager 10C travels which, of course, essentially matches the shape of Schlemm's canal (circular or segments thereof).

Referring to FIGS. 15A-15C, another device 2D for removing tissue from the eye is shown wherein the same or similar reference numbers refer to the same or similar structure. The device 2D has a tissue engager 10D mounted to an elongate shaft 6D to form a non-cutting elongated blunt probe or tissue engager 10D. The tissue engager 10D is formed by a main body 12D attached to the shaft 6D.

The shaft may be integrally formed with the guide member 15D and the tissue engager 10D. When the guide is integrally formed with the shaft 6D, the distal end of the guide member 15D is simply a distal end of the elongate shaft 6D. The wire 15D which forms the shaft 6D may have a bent portion 40 which forms the tissue engager 10D. The shaft 6D has a curved portion 11D with the bent portion 40 extending inwardly relative to the curved portion 11D by a distance 55 of 200 to 800 microns. The bent portion 40 may form an angle with the elongate shaft 6D of 10 to 150 degrees.

The elongate shaft is integrally formed with the tissue engager 10D and the guide member 15D. The elongate shaft 6D (and optionally the tissue engager 10D and the guide member 15D) may be the wire 15D having an effective radius of 40 to 400 microns, or 50-300 microns, although different sizes and shapes may be used without departing from the invention. The shaft 6D may be made of a metal such as a superelastic material (nitinol). The effective radius is the equivalent radius for a circle having the same cross-sectional area for a non-circular cross-section (such as elliptical or rectangular).

The main body 12D has a first sidewall 14D and a second sidewall 16D on opposing lateral sides of the main body 12D. The guide member 15D may extend distally from the main body 12D by a distance of 30-500 microns. The shaft 6D extends proximally from the tissue engaging element 10D and may form an angle with the advancing direction AD of greater than 135 degrees and may be 160 to 200 degrees. A central plane CP4 is defined as a plane on which the advancing direction AD lies and which includes the shaft 6D at a connection of the shaft 6D to the tissue engager 10D. The central plane CP4 may also be defined as the plane on which the advancing direction AD lies and which is positioned on a centerline of the tissue engager 10D when viewed along the advancing direction AD.

The guide member 15D has an upper surface and a lower surface with the lower surface sliding against a wall of Schlemm's canal during use. The tissue engager 10D has a height H measured perpendicular to the advancing direction AD and a width W which may be defined by any of the ranges described herein and such ranges are expressly incorporated here. The first sidewall 14D and the second sidewall 16D may have a height and a length within any of the ranges described herein and all such ranges and aspects are incorporated here.

Referring to FIGS. 16-20, another device 2E for increasing aqueous drainage in an eye is shown wherein the same or similar reference numbers refer to the same or similar structure. The device 2E has a tissue engager 10E mounted to a shaft 6E. The shaft 6E may have any of the properties of the shafts described herein and the shaft 6E is mounted to the handpiece 13 (see FIG. 1A) in the same manner and use as the shaft 6 and all such uses, features and properties are incorporated here. The tissue engager 10E engages and displaces the trabecular meshwork and is part of a main body 12E. The tissue gathers so that the tissue stretches and tears along a first sidewall 14E and a second sidewall 16E as described herein. The shaft 6E may be made of any suitable material and may be a metal including a superelastic material such as nitinol. The tissue engager 10E is coupled to an introducer 17E which may be a 0.022" stainless steel tube having a shape end to match the tissue engager 10E. The introducer 17E includes a 0.014" OD sleeve 71E.

The device 2E has a guide member 15E to guide the device 2E along Schlemm's canal. The guide member 15E may be formed by the shaft 6E as shown or could be part of the main body 12E. The main body 12E has the first sidewall 14E and the second sidewall 16E on opposing lateral sides of the main body 12E. The guide member 15E may extend distally from the main body 12E by a distance of 30-500 microns although the guide member 15E may be shorter or longer without departing from numerous aspects of the present invention. The shaft 6E extends proximally from the tissue engager 10E. A central plane CP2 is defined as a plane on which the advancing direction AD lies and which includes the shaft 6E at the connection of the shaft 6E to the main body 12E (and to the tissue engager 10E). The central plane CP2 may also be defined as the plane on which the advancing direction AD lies and the curved portion 11 of the shaft 6E. The central plane CP2 also defines the plane on which Schlemm's canal lies.

The guide member 15E has an upper surface 18E and a lower surface 20E with the lower surface 20E sliding against a wall of Schlemm's canal in use. The tissue engager 10E is the portion of the main body 12E which displaces the tissue and includes a frustoconical surface 49E, which tapers down to the guide member 15E (which may be an extension of the shaft 6E) and tapers up to a substantially tubular portion 51E of the main body 12E which also constitutes part of the tissue engager 10E. The tissue engager 10E has a height H2 measured perpendicular to the advancing direction AD which may be at least 600 microns and may be about 1000 microns. The height H2 may be at least 300 microns, at least 400 microns, at least 500 microns or may be 550-1200 microns or even 800 to 1200 microns. The tissue engager 10E also has a width W2 (measured perpendicular to the advancing direction) which may be about 560 microns. The width W2 is measured perpendicular to the advancing direction and may be at least 300 microns, at least 400 microns, or in the range of 300 to 700 microns, 450-850 microns or even 500-700 microns.

The various surfaces and dimensions described herein for all embodiments shall be defined by the view associated with particular surface or orientation. When considering a rectangular-shaped cross-section each of four defined sides may be well defined. When a circular cross-sectional shape is used, such as with device 6E, it is understood that the definition of upper surface and lower surface would subdivide the circular cross-section into two half circles. Similarly, the lateral walls would subdivide into two half circles which means that each part of the surface may define two surfaces since the surfaces are exposed in two orientations and contribute to both width and height.

The tissue engager 10E may also have a tissue engaging surface which may have a concave portion 22E when viewed perpendicular to the advancing direction AD. The tissue engaging surface also includes the frustoconical surface 49E and tubular portion 51E. The concave portion 22E has an upper lip 24E and a lower lip 26E (formed by an upper part of the frustoconical portion 49) which helps to gather the tissue as the device 2E is advanced. The upper lip 24E may form an angle A3 of less than 90 degrees, alternatively an angle of 30-70 degrees, with the advancing direction AD when viewed perpendicular to the advancing direction AD. The concave portion 22E also constitutes a recess 28E as used herein (when viewed perpendicular to the advancing direction) with the recess 28E having a depth of at least 50 microns measured perpendicular to a line extending between the upper lip and lower lip.

The first sidewall 14E and the second sidewall 16E extend on opposing lateral sides of the tissue engaging surface. The first sidewall 14E and the second sidewall 16E may have a height of 500 to 800 microns (measured perpendicular to the advancing direction AD) and a length of 180 to 220 microns (measured along the advancing direction AD) but any of the ranges described herein may be used and are incorporated here.

Figure 21:
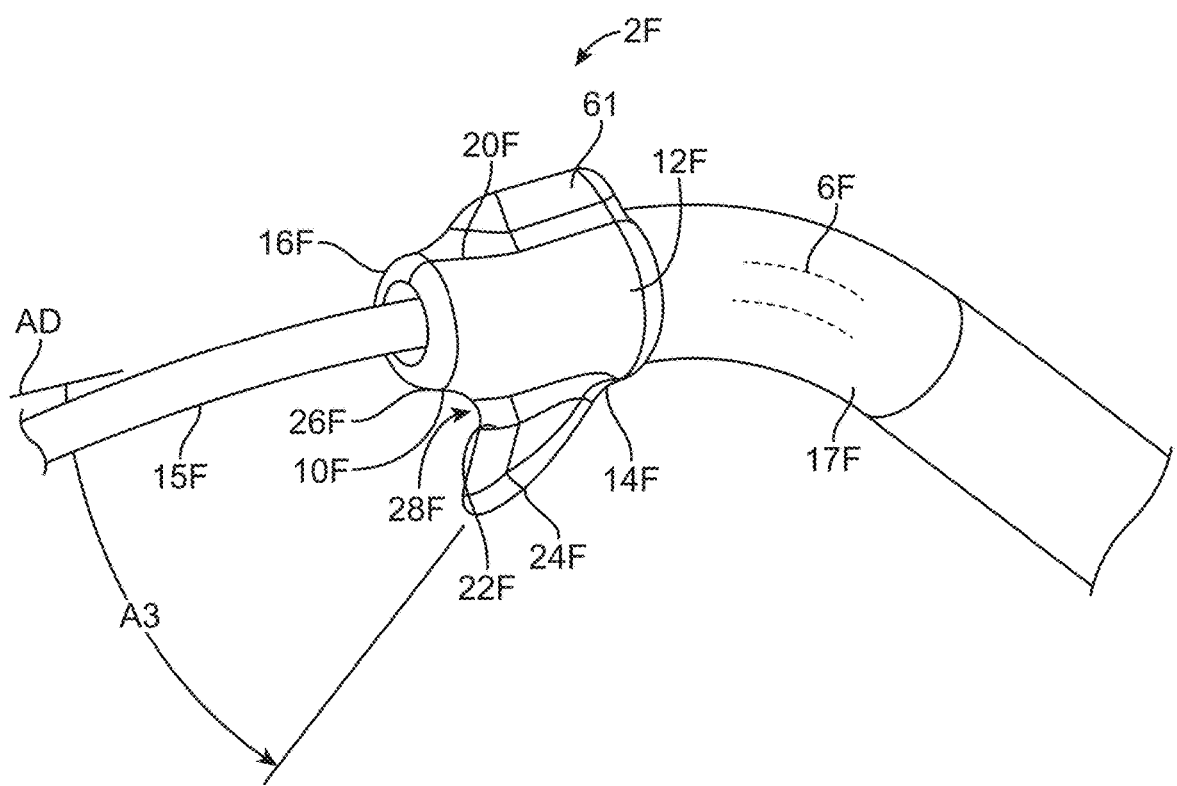
FIG. 21 shows another device for removing tissue from an eye which includes a cutting element.

Referring to FIG. 21, still another device 2F is shown for improving aqueous flow in an eye wherein the same or similar reference numbers refer to the same or similar structure and all characteristics, uses and properties of similar structure are incorporated here. The device 2F includes a main body 12F having a tissue engager 10F which is substantially similar to those described above except that it also includes a cutting element 61. The cutting element 61 cuts a circumferential slit in the canal wall as the device is advanced along the canal wall.

The device 2F includes a shaft 6F which extends through an introducer 17F and mounted to a handpiece 13 (see FIG. 1A) and operated in the manner described herein. The tissue engager 10F (formed by a main body 12F) may gather tissue so that the tissue stretches and tears along a first sidewall 14F and a second sidewall 16F as described herein. The device 2F may also operate without trabeculorhexis without departing from aspects of the present invention which may be practiced with the cutting element 61. The shaft 6F may be made of any suitable material and may be a metal, including a superelastic material such as nitinol.

The device 2F has a guide member 15F to guide the device 2F along Schlemm's canal. The guide member 15F may be formed by the shaft 6F as shown or could be part of the main body 12F. The main body 12F has the first sidewall 14F and the second sidewall 16F on opposing lateral sides of the main body 12F. The guide member 15F has an upper surface and a lower surface with the lower surface sliding against a wall of Schlemm's canal in use. The main body 12F has a torus-shaped a leading edge leading to a tubular portion. The torus-shaped leading edge tapers down to the guide member 15F and tapers up to the tubular portion.

Figure 22A:
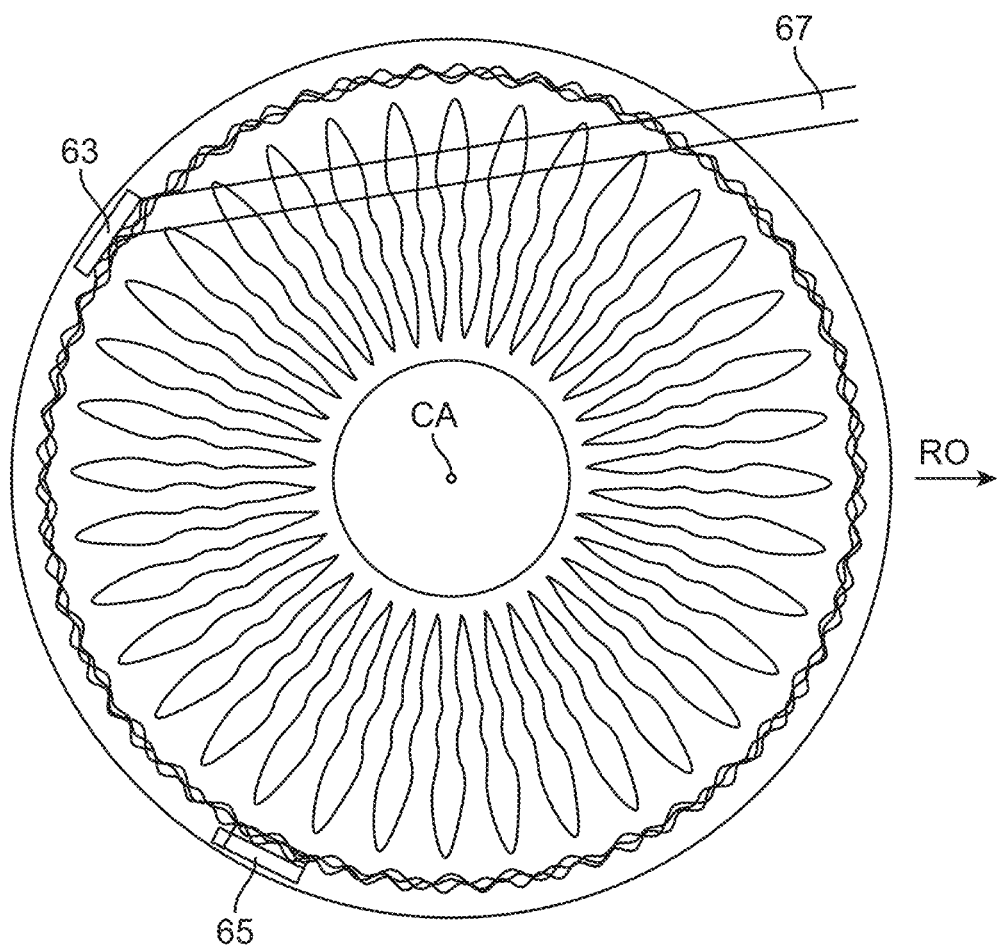
FIG. 22A shows an entry opening and a terminal opening formed through the trabecular meshwork and FIG. 22B shows the central axis CA of the eye shown in FIG. 22A.
Figure 22B:
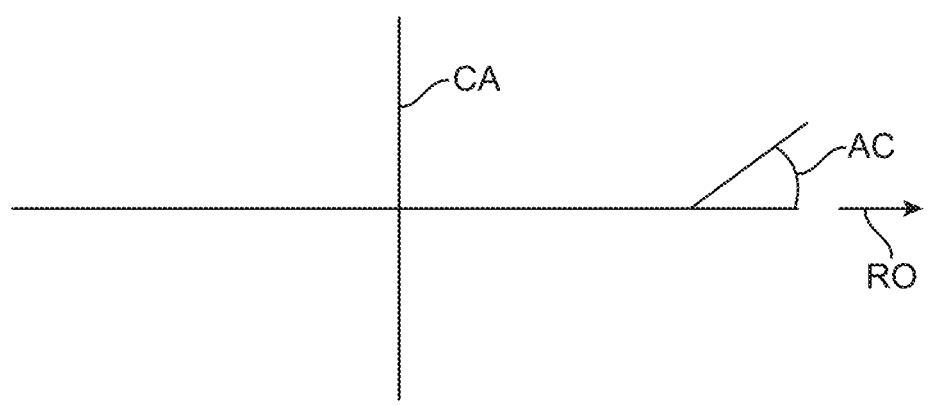

Referring to FIGS. 21, 22A and 22B, the cutting element 61 extends from a lower surface 20F of the tissue engager 10F in a radially outward direction as defined by the circular shape of the eye (and the central axis CA of the eye). The cutting element 61 is coupled to the tissue engager along the lower surface 20F which is pressed against the wall of the canal. The cutting element 61 may be oriented to form a cut which is essentially radially outward RO direction relative to the central axis of the eye. The cutting element 61 may be oriented to form a cut with an angle AC which is within 60 degrees, 30 degrees, or even within 15 degrees, of the radially outward RO direction defined by the circular shape and central axis CA of the eye.

The cutting element 61 is capable of forming a continuous cut in the wall of Schlemm's canal to increase an effective size of Schlemm's canal. The effective size is increased since the slit increases the potential enclosed volume of the canal. Any length of slit may be formed and the device is capable of forming a continuous cut through at least 45 degrees, and may be at least 90 degrees, of Schlemm's canal in use. The cutting element 61 may extend from the surface which slides against the canal wall which may help stabilize the cutting element 61. The shaft 6F is also capable of developing the spring response described herein which may also provide advantages when advancing the cutting element 61 through the canal wall. The cutting element 61 may be incorporated into any of the other devices described herein and readily positioned in the same relative position and with the same features and uses. All such combinations are expressly provided for herein and all uses and characteristics of the cutting element 61 are equally applicable to a combination with any of the other devices described herein.

The cutting element 61 also forms an elongate (in the circumferential direction) slit which increases the available surface area available for fluid transfer. The slit also effectively shortens the fluid path since the fluid path is generally radially outward and the slit is formed generally in a radially outward direction. The methods of the present invention may be also practiced without removing the trabecular meshwork in a canaloplasty procedure. The tissue engager and cutting element would be reduced in size and delivered through a cannula to form one or more circumferential slits in the radially outer (sclera) wall. The elongate slit may provide improvement in fluid flow as a primary canaloplasty therapy for the reasons discussed above.

The tissue engager 10F may also have similar structures to the other devices described herein and these similar structures are now described and all features of similar structures of any other device described herein are incorporated here. A tissue engaging surface may have a concave portion 22F when viewed perpendicular to the advancing direction AD. The concave portion 22F has an upper lip 24F and a lower lip 26F which helps to gather and compress tissue as the device 2F is advanced. The upper lip 24F may form an angle A3 of less than 90 degrees, alternatively an angle of 30-70 degrees, with the advancing direction AD when viewed perpendicular to the advancing direction AD. The concave portion 22F also constitutes a recess 28F as used herein when viewed perpendicular to the advancing direction. The first sidewall 14F and the second sidewall 16F extend from the tissue engaging surface on opposing lateral sides of the tissue engaging surface 20F. The first sidewall 14F and the second sidewall 16F may have a height, width and a length consistent with the ranges described herein which are incorporated here.

Figure 25:
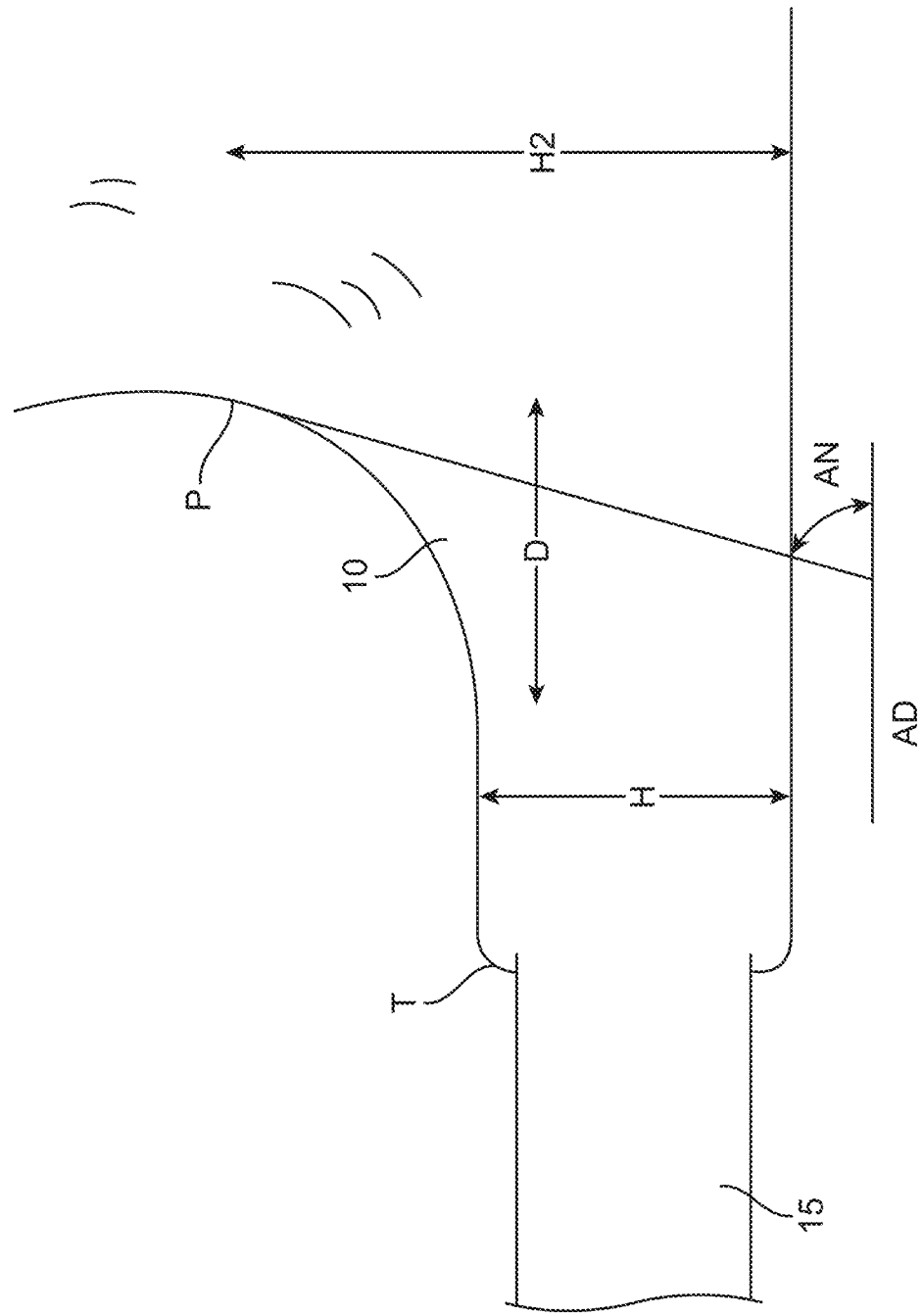
FIG. 25 shows a view of the device relating to dimensions of the tissue engager.

Referring to FIG. 25, is a schematic view of any of the devices described herein for the purpose of defining further dimensional characteristics. The tissue engager 10 may quickly gain a steep angle AN to gather, compress and push the tissue in the advancing direction AD. The tissue engager 10 may be tightly curved in this area so that the tissue engager 10 quickly gains a steep angle AN at point P in a relatively short distance D. Of course, a beveled or rounded atraumatic transition T from the guide member 15 may be desirable, however, many prior art devices use a relatively long ramped surface which tends to stretch the tissue over the ramp. Such ramps may tend to stretch the tissue between the lateral sides and apply an upward force which may increase the likelihood that the tissue separates along a single separation line between the lateral sides rather than tearing along two lateral sides to remove tissue as described herein.

The devices of the present invention may have a relatively small height H when the tissue engager 10 begins to form a relatively steep angle to gather, compress and subsequently tear the tissue along the lateral sides. To this end, the main body 12 extends proximally from the guide member 15 and has a height H which increases in proximal direction. When the increasing height reaches 0.014 inch the tissue engager 10 increases to an angle AN of 60 degrees relative to the advancing direction within a distance D measured in the advancing direction of 0.035 inch. An alternative range is when the height H reaches 0.012 inch that the angle AN reaches 80 degrees within 0.030 inch or when the height H reaches 0.010 inch and the angle AN reaches 90 degrees within 0.025 inch. Stated another way, the height H2 may be no more than 0.035 when the tissue engager 10 forms an angle of 80 degrees with the advancing direction AD or no more than 0.027 when the tissue engager 10 forms an angle of 90 degrees with the advancing direction.

The width W2 (see FIG. 20) of the tissue engager 10 may be somewhat moderate in the area where the tissue is gathered. The tissue engager 10 is curved to gather tissue while permitting enough lateral room for the tissue to "drape" around the tissue engager 10 and tear along the two sides. The width W2 may be 0.010 to 0.0030 inch when the tissue engager 10 increases to an angle AN of 80 degrees relative to the advancing direction or may be 0.012 to 0.0025 inch when the tissue engager 10 increases to an angle AN of 90 degrees relative to the advancing direction.

Figure 23:
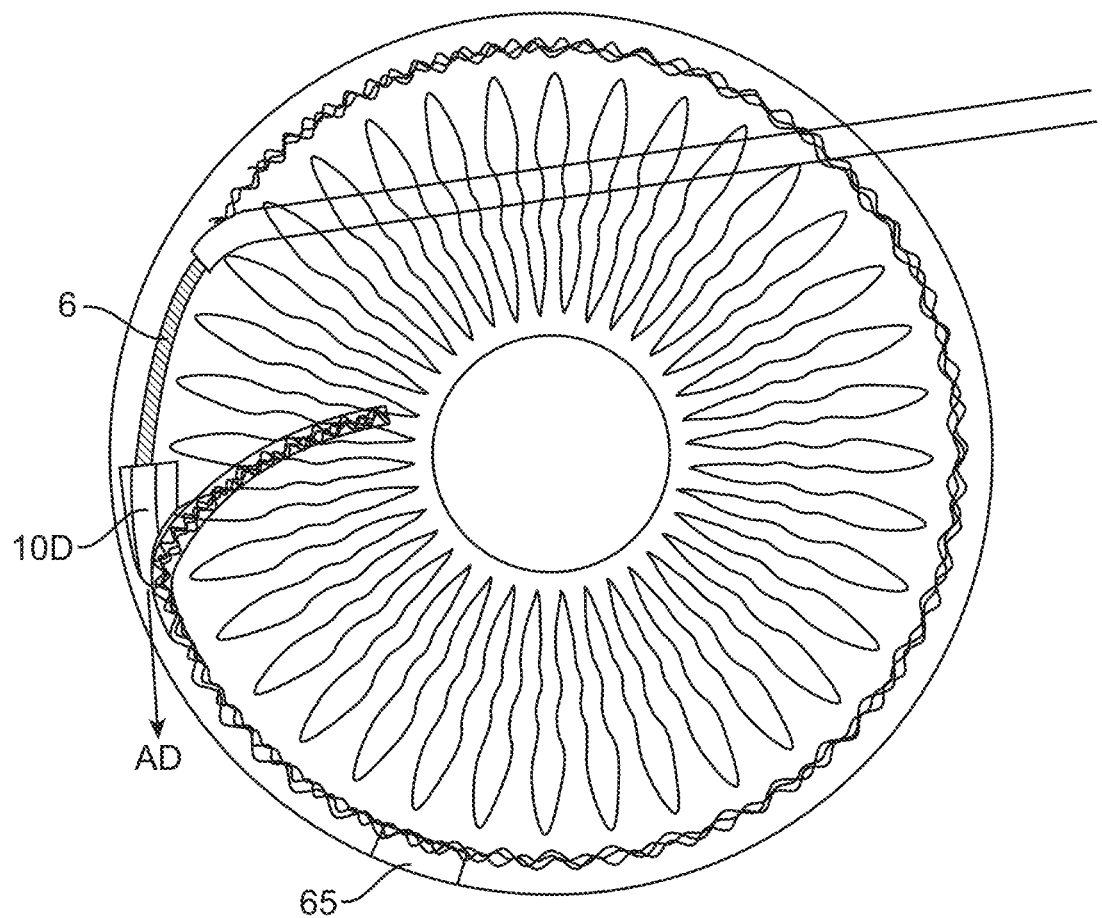
FIG. 23 shows the device introduced into the entry opening and advanced towards the terminal opening.

Use of the devices 2 and 2A-2F is now described with reference to the device 2D and FIG. 22A and FIG. 23. The elongate shaft 6D is advanced longitudinally from the introducer 17 to advance the tissue engager 10D through the trabecular tissue in the following manner. The device 6D is introduced into the eye ab interno (see FIG. 16). An entry opening 63 and a first terminal opening 65 are formed through the trabecular meshwork to Schlemm's canal using a conventional bladed instrument 67 (see FIG. 22A). The device 2D is then introduced into the entry opening 63 with the introducer extending into the entry opening 63 and the device 2D is then advanced toward the first terminal opening 65 by extending the shaft 6 from the handpiece 13 (FIG. 1). As the tissue engager 10D is advanced, the flexible, curved shaft changes the orientation of tissue engager to conform to Schlemm's canal. In this manner, the user may not be required to substantially change the orientation or position of the handpiece as the tissue engager is advanced.

When the tissue engager reaches the first terminal opening 65, a first strip of tissue has been released and removed to expose a portion of a wall of Schlemm's canal. The device 6D may be used to strip another portion of the trabecular meshwork to expose more of Schlemm's canal by forming a second terminal opening and advancing the tissue engager to the second terminal opening. The entry opening is created by removing or incising the trabecular meshwork to the outer wall of Schlemm's canal or through Schlemm's canal to expose the sclera. The strip of trabecular meshwork released by the present devices may also be parted off with a separate device or with the devices themselves (by cutting or tearing) as now described.

Figure 24:
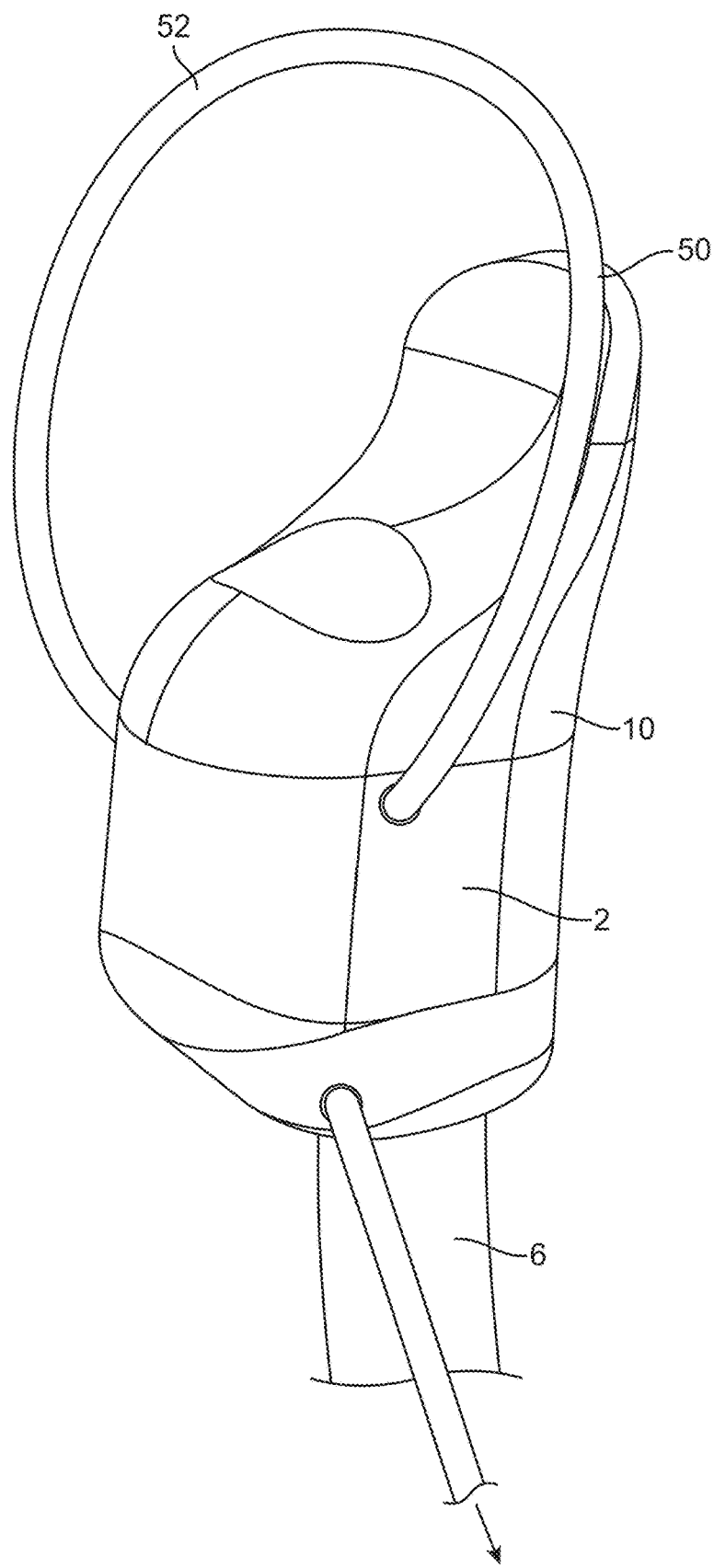
FIG. 24 shows a device including a part-off mechanism.

Referring to FIG. 24, the device 2 may include a part-off mechanism 50 to separate the tissue strip from the native tissue. The part-off mechanism 50 may be a loop 52 of material through which the tissue strip is initially guided. The loop is kept in the open position of FIG. 24 until it is desired to part-off the tissue at which time the loop is cinched (closed) to cut the tissue strip. When the part-off mechanism is provided it may be unnecessary to form the terminal opening as part of the procedure. The part-off mechanism may also be carried out with a sharp cutting implement or with a separate device without departing from numerous aspects of the present invention. The part-off mechanism has an actuator coupled to the handpiece with the part-off mechanism separating the tissue strip from native tissue upon actuation. The loop of material may be a superelastic material such as nitinol. Alternatively, a suture or a polymeric filament or any other suitable filament or wire may be used. The tissue strip extends through the loop as the tissue engager is advanced. The loop is closed to cut the tissue strip upon actuation of the actuator. The device may also include a suction lumen coupled to the handpiece for removing the tissue displaced and released by the device. The step of parting off the tissue strip may be unnecessary, of course, when forming the terminal opening.

As used herein, the term "displace tissue" includes both blunt engagement to move the tissue but also cutting the tissue to move the tissue in the path of the tissue engager. The terms "gather" tissue and "gathering" tissue shall mean that tissue collects and bunches up in front of the tissue engager. The gathered tissue may be somewhat compressed as it collects ahead of the device. Displacement of this gathered tissue advantageously rips/tears/shears the tissue along both lateral sides so that a strip of material is being freed from the native tissue. Use of a cutting element may result in a slit being formed without meaningful removal of material. Similarly, use of a rounded tube or element may result in simply tearing the trabecular meshwork open along a seam without meaningful removing material. The ability of the devices of the present invention to gather tissue does not require the device to gather all of the tissue being removed. The gathered tissue may slide to one side or the other or "over" the tissue engager so that the tissue engager gathering a different part of the trabecular meshwork and tearing/ripping tissue free by displacing the newly gathered different part of the trabecular meshwork. The present invention gathers tissue corresponding to the width of the tissue engaging element while a rounded tube (or a cutting element) are not capable of gathering tissue in this manner.

The advancing direction as used herein is defined as a local vector which is essentially a tangent to the circular shape of the Schlemm's canal. As such, the advancing direction essentially follows the curvature of the Schlemm's canal rather than defining a single direction. All compatible features of any embodiment shall be interchangeable with any other embodiment and all such combinations are expressly incorporated herein. For example, the non-circular cross-sectional shape for the elongate shaft may be used with (and claimed with) any of the other embodiments described herein and the dimensions and characteristics of the any recess may be attributed to any other recess. As another example, the shape, stiffness and properties of the shaft (such as shaft 6) described in any embodiment may be used with any of the devices described herein and all such uses are incorporated herein whether expressly described or not. Finally, the dimensions and distances shall be deemed average values for a particular quantity as necessary.

In addition, the non-cutting probe and or the tissue micro-disruptor/trabeculorhexis element may both have tissue modulating surface elements on their outer surface which can engage and/or modulate the surface of the external canal wall. For example, such elements may include micro-abrasive surface for canal wall cleaning, debridement and/or thinning. Further embodiments of a combined trabeculorhexis-canaloplasty device whereby in addition to the trabeculorhexis configuration, the device has features designed to change, modulate, abrade, shave, thin, microperforate the external/contralateral-to-the-TM canal wall. This can be achieved by a modified surface architecture of the guide-probe and/or the tissue disruptor and/or the flexible shaft with abrasive non-smooth surface including but not limited to a grating configuration, notching and other surface elements designed to treat and modify the surface the canal wall surface during movement of the device along the contour of the canal. This combined trabeculorhexis-canaloplasty procedure will not only disinsert and remove the TM, but also can improve and change the anatomy of the remaining canal wall for additional improvement of aqueous outflow. In addition, a further embodiment where the surface of such ab-interno device (guide-probe and tissue disruptor) can be coated with a hemostatic coating (e.g. silver nitrate) which can reduce bleeding during the procedure. The device is preferably introduced ab interno but aspects of the present invention may be practiced with ab externo approach without departing from the scope of the invention. As the device of the present invention is moved to tear tissue, the device does so preferably without cutting or ablating the tissue. Of course, cutting devices and even a cutting element with the devices of the present invention may be provided without departing from numerous aspects of the present invention. The present invention may also be practiced without any implantable structure (including no implantable structures coupled to the handpiece) left in the eye. Of course, aspects of the present invention could be practiced in conjunction with a shunt or stent-like structure without departing from aspects of the present invention.

As used herein, the terms are often used with reference to a view of the device in use and may be modified as described below to provide further clarification of these term. The term advancing direction may be modified with the term "which is oriented in a tangential direction with respect to the circular shape of the eye." The term height may be modified with the term "which is radially oriented with respect to the circular shape of the eye". Similarly, the term "width" may be modified with the term "which is oriented perpendicular to the advancing direction and the height" or with the term "oriented parallel to a central axis of the eye". Finally, the terms upper or upper surface and lower or lower surface may be modified with the terms "which is oriented on a radially inner surface with respect to the circular shape of the eye" and "oriented on a radially outer surface with respect to the circular shape of the eye", respectively. The above referenced terms apply to circular, tubular and frustoconical shapes equally.

The devices and methods have been described with reference to preferred embodiments, however, various modifications may be made within the scope of the present invention. For example, aspects of the flexible shaft may be used with a cutting or ablating element or the device may be used with a rigid shaft with an articulated head without departing from the trabeculorhexis aspects of the present invention.

What is claimed is:

1. A method of disrupting tissue in an eye, said method comprising:
   inserting a distal portion of a device into an anterior chamber of the eye, said distal portion comprising an elongate, flexible shaft, a distal guide member and a tissue disruptor coupled to said shaft proximally of said distal guide member, said tissue disruptor comprising a protrusion extending radially inwardly from the shaft and a cutting edge disposed radially outwardly from the shaft said protrusion comprising a blunt tissue-engaging surface without any cutting element;
   positioning said distal portion adjacent a trabecular meshwork of the eye;
   inserting the distal guide member through said trabecular meshwork and into a portion of Schlemm's Canal; and
   advancing the distal guide member along Schlemm's Canal away from said portion of Schlemm's Canal, wherein as the distal guide member advances along Schlemm's Canal, said tissue-engaging surface of said protrusion bluntly tears trabecular meshwork tissue to remove a portion of an inner wall of Schlemm's Canal and, at the same time, said cutting edge cuts an outer wall of Schlemm's Canal.

2. The method of claim 1, wherein said device further comprises an introducer tube comprising a curved or bent distal portion and a lumen, and
   wherein said inserting said distal portion of said device comprises inserting said curved or bent distal portion of said introducer tube into said anterior chamber, and further wherein a portion of said shaft is within said lumen of said curved or bent portion during said inserting.

3. The method of claim 2, wherein said advancing said distal guide member along Schlemm's Canal comprises extending said shaft from said introducer tube to advance said distal guide member along Schlemm's Canal.

4. The method of claim 3, further comprising varying a stiffness of the shaft by changing a length of the shaft extending from the introducer tube.

5. The method of claim 4, where said stiffness of the shaft varies by at least a factor of 10 as the length of the shaft extending from the introducer tube increases.

6. The method of claim 3, further comprising moving a slide to extend said shaft from said introducer tube to advance said distal guide member along Schlemm's Canal.

7. The method of claim 6, further comprising retracting the slide to retract the distal guide member towards said introducer tube.

8. The method of claim 3, wherein as said shaft extends from said introducer tube, said shaft develops a spring-load.

9. The method of claim 3, wherein as said shaft extends from said introducer tube, said shaft applies a radially outward force against an outer wall of Schlemm's Canal.

10. The method of claim 2, wherein during said inserting into said anterior chamber, said guide member and said tissue disruptor remain distal of said curved or bent portion of said introducer tube.

11. The method of claim 1, wherein said device further comprises a proximal portion that remains outside the eye.

12. The method of claim 11, wherein said proximal portion comprises an actuator operatively coupled to said shaft, said method further comprising operating said actuator to advance said distal guide member along Schlemm's Canal.

13. The method of claim 12, wherein said actuator comprises a slide, said method further comprising moving the slide to advance said distal guide member along Schlemm's Canal.

14. The method of claim 1, wherein said shaft comprises a resiliency.

15. The method of claim 14, wherein said shaft comprises nitinol.

16. The method of claim 14, wherein said resiliency of said shaft causes said distal guide member to slide along said inner wall or an outer wall of Schlemm's Canal during said advancing along Schlemm's Canal.

17. The method of claim 1, wherein said distal portion of said device is inserted into said anterior chamber ab interno.

18. The method of claim 1, wherein said distal guide member comprises a blunt, distal portion of said shaft, and further wherein said shaft comprises a wire.

19. The method of claim 1, further comprising disinserting said trabecular meshwork tissue from attachment to other eye tissue with said blunt tissue-engaging surface of said tissue disruptor as said distal guide member advances along Schlemm's Canal.

20. The method of claim 1, wherein said cutting said outer wall of Schlemm's Canal forms a continuous slit in the outer wall of Schlemm's Canal.

21. The method of claim 1, wherein said cutting said outer wall of Schlemm's Canal increases an effective size of Schlemm's Canal.

22. The method of claim 1, further comprising removing said distal portion of said device from the eye without deploying or providing any implantable structure with the device.

23. The method of claim 1, wherein a portion of said shaft has a curved shape with a radius of curvature of 5 to 9 mm.

24. The method of claim 1, wherein said advancing the distal guide member along Schlemm's Canal comprises advancing the distal guide member around 30 to 120 degrees of a circumference of Schlemm's Canal.

25. The method of claim 1, wherein said outer wall of Schlemm's Canal comprises sclera, and further wherein, as said distal guide member advances along Schlemm's Canal, said cutting edge of said tissue disruptor forms an elongate slit in said outer wall to thin said sclera.

26. The method of claim 1, wherein said advancing along Schlemm's Canal comprises following a circumferential contour of Schlemm's Canal.

27. The method of claim 1, wherein, as said distal guide member advances along Schlemm's Canal, said elongate flexible shaft applies a radially outward force against said outer wall of Schlemm's Canal.

28. A method of performing a procedure on a patient's eye, said method comprising:
   advancing along Schlemm's Canal a portion of a medical instrument inserted at least in part into Schlemm's Canal, and
   during said advancing along Schlemm's Canal, both:
   bluntly tearing or disinserting, without cutting, trabecular meshwork tissue; and, at the same time,
   cutting, slitting, abrading, shaving, debriding or microperforating an outer wall of Schlemm's Canal.

29. The method of claim 28, wherein said procedure is performed without deploying or providing any implantable structure.

30. The method of claim 28, wherein said portion of said medical instrument comprises a guide member inserted into Schlemm's Canal.

* * * * *